(12) United States Patent
Shuttleworth et al.

(10) Patent No.: US 10,533,003 B2
(45) Date of Patent: Jan. 14, 2020

(54) POLYHETEROARL HISTONE DEACETYLASE INHIBITORS AND THEIR USE IN THERAPY

(71) Applicant: Karus Therapeutics Limited, Oxfordshire (GB)

(72) Inventors: Stephen Joseph Shuttleworth, Oxfordshire (GB); Alexander Richard Liam Cecil, Oxfordshire (GB); Somhairle MacCormick, Oxfordshire (GB); William John Nodes, Oxfordshire (GB); Cyrille Davy Tomassi, Oxfordshire (GB); Franck Alexandre Silva, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 15/522,191

(22) PCT Filed: Oct. 29, 2015

(86) PCT No.: PCT/GB2015/053256
§ 371 (c)(1),
(2) Date: Apr. 26, 2017

(87) PCT Pub. No.: WO2016/067038
PCT Pub. Date: May 6, 2016

(65) Prior Publication Data
US 2017/0313698 A1 Nov. 2, 2017

(30) Foreign Application Priority Data
Oct. 29, 2014 (GB) .................................. 1419264.5

(51) Int. Cl.
| A61K 31/497 | (2006.01) |
| A61K 31/506 | (2006.01) |
| C07D 471/04 | (2006.01) |
| C07D 401/14 | (2006.01) |
| C07D 405/14 | (2006.01) |
| C07D 413/14 | (2006.01) |

(52) U.S. Cl.
CPC .......... *C07D 471/04* (2013.01); *A61K 31/497* (2013.01); *A61K 31/506* (2013.01); *C07D 401/14* (2013.01); *C07D 405/14* (2013.01); *C07D 413/14* (2013.01)

(58) Field of Classification Search
None
See application file for complete search history.

(56) References Cited

U.S. PATENT DOCUMENTS

| 4,017,500 | A | 4/1977 | Mayer et al. |
| 7,022,840 | B2 | 4/2006 | Kobuke et al. |
| 8,748,458 | B2 | 6/2014 | Shuttleworth et al. |
| 9,200,007 | B2 | 12/2015 | Shuttleworth et al. |
| 9,266,879 | B2 | 2/2016 | Shuttleworth et al. |
| 9,340,503 | B2 | 2/2016 | Shuttleworth et al. |
| 9,676,765 | B2 | 6/2017 | Shuttleworth et al. |
| 9,862,685 | B2 | 1/2018 | Shuttleworth et al. |
| 10,150,763 | B2 | 12/2018 | Shuttleworth et al. |
| 2002/0099210 | A1 | 7/2002 | Alexander et al. |
| 2002/0151544 | A1 | 10/2002 | Hayakawa et al. |
| 2004/0106787 | A1 | 6/2004 | Kobuke et al. |
| 2004/0235888 | A1 | 11/2004 | Yamamori et al. |
| 2006/0239909 | A1 | 10/2006 | Anderson et al. |
| 2007/0135466 | A1 | 6/2007 | Ledeboer et al. |
| 2008/0125440 | A1 | 5/2008 | Cai et al. |
| 2008/0207729 | A1 | 8/2008 | Pisano et al. |
| 2008/0221112 | A1 | 9/2008 | Yamamori et al. |
| 2011/0201608 | A1 | 8/2011 | Hoffmann et al. |
| 2011/0305729 | A1 | 12/2011 | Shuttleworth et al. |
| 2012/0171199 | A1 | 7/2012 | Dotson et al. |
| 2012/0178737 | A1 | 7/2012 | Shuttleworth et al. |
| 2013/0109688 | A1 | 5/2013 | Shuttleworth et al. |
| 2014/0235671 | A1 | 8/2014 | Shuttleworth et al. |
| 2014/0378385 | A1 | 12/2014 | Raje et al. |

(Continued)

FOREIGN PATENT DOCUMENTS

| CN | 101228161 A | 7/2008 |
| CN | 101663276 A | 3/2010 |

(Continued)

OTHER PUBLICATIONS

Bush; Circulation Research 2010, 106, 272-284. (Year: 2010).

(Continued)

*Primary Examiner* — Samantha L Shterengarts
(74) *Attorney, Agent, or Firm* — Goodwin Procter LLP

(57) ABSTRACT

The present invention is a compound having the following formula: or a pharmaceutically acceptable salt thereof, wherein e.g. L and Y are each independently an optionally substituted 6-membered nitrogen-containing heteroaryl; M is an optionally substituted 5- to 10-membered heteroaryl; W is a zinc-binding group; each $R_2$ is independently hydrogen or $C_1$-$C_6$ alkyl; and $R_3$ is an aryl or heteroaryl. The compounds are useful as histone deacetylase (HDAC) inhibitors.

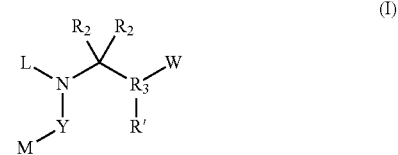

7 Claims, No Drawings

(56) References Cited

U.S. PATENT DOCUMENTS

| | | | |
|---|---|---|---|
| 2015/0080395 A1 | 3/2015 | Shuttleworth et al. |
| 2015/0361074 A1 | 12/2015 | Shuttleworth et al. |
| 2016/0096804 A1 | 4/2016 | Shuttleworth et al. |
| 2016/0108057 A1 | 4/2016 | Shuttleworth et al. |
| 2017/0313712 A1 | 11/2017 | Shuttleworth et al. |
| 2018/0086750 A1 | 3/2018 | Shuttleworth et al. |
| 2018/0170876 A1 | 6/2018 | Shuttleworth et al. |

FOREIGN PATENT DOCUMENTS

| | | |
|---|---|---|
| CN | 104125946 A | 10/2014 |
| EP | 0226099 A2 | 6/1987 |
| EP | 0509400 A1 | 10/1992 |
| EP | 0556396 A1 | 8/1993 |
| EP | 0887348 A1 | 12/1998 |
| EP | 1277738 A1 | 1/2003 |
| EP | 1724267 A1 | 11/2006 |
| EP | 2508510 A1 | 10/2012 |
| EP | 2813506 A1 | 12/2014 |
| JP | H11302254 A | 11/1999 |
| JP | 2002/255964 A | 9/2002 |
| JP | 2003 313126 A | 11/2003 |
| JP | 2004-002826 A | 1/2004 |
| JP | 2008542428 A | 11/2008 |
| JP | 2012508223 A | 4/2012 |
| JP | 2001139550 A | 5/2013 |
| JP | 2014503535 A | 2/2014 |
| WO | WO-1997/40017 A2 | 10/1997 |
| WO | WO-99/00381 A1 | 1/1999 |
| WO | WO-2001/083456 A1 | 11/2001 |
| WO | WO-2002/002551 A1 | 1/2002 |
| WO | WO-2002/034748 A1 | 5/2002 |
| WO | WO-2002/085400 A1 | 10/2002 |
| WO | WO-2003/075929 A1 | 9/2003 |
| WO | WO-2004/072047 A1 | 8/2004 |
| WO | WO-2005-118539 | 12/2005 |
| WO | WO-2006/037335 A2 | 4/2006 |
| WO | WO-2006/046035 A1 | 5/2006 |
| WO | WO-2006/088949 | 8/2006 |
| WO | WO-2006/127587 A1 | 11/2006 |
| WO | WO-2006/131484 | 12/2006 |
| WO | WO-2007/050348 A2 | 5/2007 |
| WO | WO-2007/084667 A2 | 7/2007 |
| WO | WO-2007/085540 A1 | 8/2007 |
| WO | WO-2007/122410 A1 | 11/2007 |
| WO | WO-2007/127183 A1 | 11/2007 |
| WO | WO-2008/007780 A1 | 1/2008 |
| WO | WO-2008/033746 | 3/2008 |
| WO | WO-2008/055068 A2 | 5/2008 |
| WO | WO-2008/062201 A1 | 5/2008 |
| WO | WO-2008/094992 A2 | 8/2008 |
| WO | WO-2008/137270 A1 | 11/2008 |
| WO | WO-2008/139987 A1 | 11/2008 |
| WO | WO-2008/145688 A2 | 12/2008 |
| WO | WO-2008/150827 A1 | 12/2008 |
| WO | WO-2009/063240 A1 | 5/2009 |
| WO | WO-2009/137462 A2 | 11/2009 |
| WO | WO-2010/015520 A1 | 2/2010 |
| WO | WO-2010/037765 A2 | 4/2010 |
| WO | WO-2010/052569 A2 | 5/2010 |
| WO | WO-2010/086646 A1 | 8/2010 |
| WO | WO-2011/021038 A1 | 2/2011 |
| WO | WO-2012/045804 A1 | 4/2012 |
| WO | WO-2012/082997 A1 | 6/2012 |
| WO | WO-2012/106343 A1 | 8/2012 |
| WO | WO-2012/136722 A1 | 10/2012 |
| WO | WO-2013/052110 A1 | 4/2013 |
| WO | WO-2013/052613 A1 | 4/2013 |
| WO | WO-2013/088404 A1 | 6/2013 |
| WO | WO-2013/095060 A1 | 6/2013 |
| WO | WO-2013/132270 A1 | 9/2013 |
| WO | WO-2014/032019 A2 | 2/2014 |
| WO | WO-2014/072714 A1 | 5/2014 |
| WO | WO-2014/072937 A1 | 5/2014 |
| WO | WO-2014/100227 A1 | 6/2014 |
| WO | WO-2014/139465 A1 | 9/2014 |
| WO | WO-2014/153280 A1 | 9/2014 |
| WO | WO-2014/181137 A1 | 11/2014 |
| WO | WO-2015/121657 A1 | 8/2015 |
| WO | WO-2016/031815 A1 | 3/2016 |
| WO | WO-2016/067038 A1 | 5/2016 |
| WO | WO-2016067040 A1 | 5/2016 |
| WO | WO-2017/208032 A1 | 12/2017 |
| WO | WO-2017/222950 A1 | 12/2017 |
| WO | WO-2017/222951 A1 | 12/2017 |
| WO | WO-2017/222952 A1 | 12/2017 |

OTHER PUBLICATIONS

Dietz; Pharmacological Research 2010, 62, 11-17. (Year: 2010).
Grayson; Molecular Pharmacology Feb. 2010, 77, 126-135. (Year: 2010).
Kantharaj; "Histone Deacetylase Inhibitors as Therapeutic Agents for Cancer Therapy: Drug Metabolism and Pharmacokinetic Properties" Chapter 5: Drug Development—A Case Study Based Insight into Modern Strategies, pp. 101-120, Intech (Dec. 2011). (Year: 2011).
Pang; Journal of Pharmacology and Experimental Therapeutics Nov. 2010, 335, 266-272. (Year: 2010).
Xu; Oxidative Medicine and Cellular Longevity 2011, 5 pages. doi: 10.1155/2011/143269 (Year: 2011).
Uno; "N2-N1 Migration of s-Triazinyl Group in the Reaction of N1-Acetyl-N2-(s-triazinyl)alkylenediamines", Bulletin of the Chemical Society of Japan, 1973, 46(7), 2257-8.
U.S. Appl. No. 13/145,250, Scriptaid Isosteres and Their Use in Therapy, filed Aug. 30, 2011, Issued as U.S. Pat. No. 8,748,458 on Jun. 10, 2014.
U.S. Appl. No. 14/266,197, Scriptaid Isosteres and Their Use in Therapy, filed Apr. 30, 2014, Issued as U.S. Pat. No. 9,340,503 on May 17, 2016.
U.S. Appl. No. 15/095,829, Scriptaid Isosteres and Their Use in Therapy, filed Apr. 11, 2016, Pending.
U.S. Appl. No. 14/441,401, Novel Histone Deacetylase Inhibitors and Their Use in Therapy, filed May 7, 2015, Issued as U.S. Pat. No. 9,676,765 on Jun. 13, 2017.
U.S. Appl. No. 15/589,491, Novel Histone Deacetylase Inhibitors and Their Use in Therapy, filed May 8, 2017, Pending.
U.S. Appl. No. 14/890,331, Novel Histone Deacetylase Inhibitors, filed Nov. 10, 2015, Allowed Published as US 2016-0096804 on Apr. 7, 2016.
U.S. Appl. No. 15/667,069, Novel Histone Deacetylase Inhibitors, filed Aug. 2, 2017, Pending.
U.S. Appl. No. 15/522,188, Diheteroaryl Histone Deacetylase Inhibitors and Their Use in Therapy, filed Apr. 26, 2017, Pending.
Alvarez-Rua C et al., 'Multiple Hydrogen Bonds and Tautomerism in Naphthyridine Derivatives,' New J Chem, May 7, 2004 (May 7, 2004)(ePub), 28:700-7.
Anonymous, 'Abstract No. 2009:1018972 CAPLUS,' for 'Lett Drug Des Disc, (2009), 6(4):268-77,' STN CA Caesar Accession No. 1028, Nov. 17, 2015 (Nov. 17, 2015), CAplus Chemical Abstract Service, American Chemical Society, Columbus, OH (Publ), pp. 1-2 XP-002751577
Anonymous, 'CAS Registration No. RN-1257852-06-4 for Glycine, N-1H-imadazol-1-yl-N-3-pyridazinyl,' Dec. 29, 2010 (Dec. 29, 2010), CAS Registry, Chemical Abstracts Service, American Chemical Society, Columbus, OG (Publ), pp. 1, XP-002751578.
Anonymous, Chemcats, Accession No. 0056415163, for '1,6-Naphthyridine, 7-(3-methylphenyl)-5-(4-morpholinyl)-' Apr. 22, 2011 (Apr. 22, 2011), CAS Registry No. 1214393-37-9, Chemical Abstracts Service, American Chemical Society, Columbus, OH (publ), pp. 1, XP-002643660.
Anonymous, Chemcats, Accession No. 0056415178, for '1,6-Naphthyridine, 5-(4-morpholinyl)-7-(2-pyridinyl)-,' Apr. 22, 2011 (Apr. 22, 2011), CAS Registry No. 1214438-02-4, Chemical Abstracts Service, American Chemical Society, Columbus, OH (Publ), pp. 1, XP-002643660.
Anonymous, PubChem, '3-(1H-Indol-3-yl)-3-(pyridin-4-yl)propionic acid—Compound Summary,' CID 4715104, AC1NFWP0,

(56) References Cited

OTHER PUBLICATIONS

MolPort-000-861-678, BBL022406, STK895679, AKOS000266205, MCULE-7014658967, 3-(1H-indol-3-yl)-3-pyridin-3-ylpropanoic acid, Sep. 17, 2005 (Sep. 17, 2005), National Center for Biotechnology information, U.S. National Library of Medicine, Bethesda, MD (Publ), pp. 1-6 XP-002718389.

Anonymous, PubChem, '3-(1H-Indol-3-yl)-3-pyridin-4-yl-propienic acid—Compound,' CID 3157817, ST073698 3-(1H-indol-3-yl)-3-pyridin-4-yl)propanoic acid, 3-(1H-indol-3-yl)-3-(pyridin-4-yl)propanoic acid, Aug. 10, 2005 (Aug. 10, 2005), National Center for Biotechnology Information, U.S. National Library of Medicine, Bethesda, MD (Publ), pp. 1-7 XP-002718387.

Anonymous, PubChem, 'AC1LLZ4B—Compound Summary,' CID 1092973, (3S)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718385.

Anonymous, PubChem, 'AC1LLZ4D—Compound Summary,' CID 1092974, (3R)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718386.

Anonymous, PubChem, 'CID 40480236—Compound Summary,' CID 40480236, (3R)-3-(1H-indol-3-yl)-3-pyridin-3-ylpropanoic acid, May 30, 2009 (May 30, 2009), National Center for Biotechnology Information, U.S. National Lrbrary of Medicine, Bethesda, MD (Publ), pp. 1-4 XP-002718391.

Anonymous, PubChem, 'ethyl 2 [pyridine-4-yl(pyrrol-1-yl)amino]acetate; hydrochloride,' CID 67857985, Nov. 30, 2012 (Nov. 30, 2012), National Center for Biotechnology Information, U.S. National Library of Medicine, Bethesda, MD (Publ), pp. 1-5 XP-002718393.

Anonymous, PubChem, 'SureCN2072816—Compound Summary,' CID 58088407, 3-(4-methoxy-1H-indol-3-yl)-3-pyridine-4-ylpropanoic acid, Aug. 19, 2012 (Aug. 19, 2012), National Center for Biotechnology Information, U.S. National Library of Medicine, Bethesda, MD (Publ), pp. 1-5 XP-002718392.

Anonymous, PubChem, 'SureCN9469183—Compound Summary,' CID 14373294, ethyl 2-[pyridine-4-yl(pyrrol-1-yl)amino]acetate, Feb. 9, 2007 (Feb. 9, 2007), National Center for Biotechnology Information, U.S. National Library of Medicine, Bethesda, MD (Publ), pp. 1-5 XP-002718390.

Assem el-SK et al., 'Effects of a Section of Histone Deacetylase Inhibitors on Mast Cell Activation and Airway and Colonic Smooth Muscles Contraction,' Int Immunopharmacol, Dec. 20, 2008 (Dec. 20, 2008) Sep. 19, 2008 (Sep. 19, 2008)(ePub), 8(13-14):1793-801.

Bouchecareilh M et al., 'Histone Deactylase Inhibitor (HDACi) Suberoylanilide Hydroxamic Acid (SAHA)-Mediated Correction of alpha1-Antitrypsin Deficiency,' J Biol Chem, Nov. 2, 2012 (Nov. 2, 2012) Sep. 20, 2012 (Sep. 20, 2012)(ePub), 287(45):38265-78.

Bruijnincx PC et al., 'Modeling the 2-His-1-carboxylate Facial Triad: iron-catecholato Complexes as Structural and Functional Models of the Extrodiol Cleaving Dioxygenases,' J Am Chem Soc, Feb. 28, 2007 (Feb. 28, 2007) Feb. 1, 2007 (Feb. 1, 2007)(ePub), 129(8):2275-86.

Ciarlo E et al., 'Epigenetics in Sepsis: Targeting Histone Deacetylases,' Int J Antimicrob Agents, Jun. 2013 (Jun. 2013) May 9, 2013 (May 9, 2013)(ePub), 42(Supp):S8-12.

Clarke JD et al., 'Differential Effects of Sulforaphane on Histone Deacetylases, Cell Cycle Arrest and Apoptosis in Normal Prostate Cells Versus Hyperplastic and Cancerous Prostate Cells,' Mol Nutr Food Res, Jul. 2011 (Jul. 2011) Mar. 4, 2011 (Mar. 4, 2011)(ePub), 55(7):999-1009.

Crisanti MC et al., 'The HDAC Inhibitor Panobinostat (LBH589) Inhibits Mesothelioma and Lung Cancer Cells in vitro and in vivo with Particular Efficacy for Small Cell Lung Cancer,' Mol Cancer Ther, Aug. 2009 (Aug. 2009) Aug. 11, 2009 (Aug. 11, 2009)(ePub), 8(8):2221-31.

Cuadro AM et al., 'Synthesis of Highly Stabilised Ylides from N-[2-(1,3-Bensazolymethyl)] Pyridinium Salts,' Tetrahedron, Jan. 1990 (Jan. 1990), 46(17):6033-46.

Djabali K and Christiano AM, 'Hairless Contains a Novel Nuclear Matrix Targeting Signal and Associates with Histone Deacetylase 3 in Nuclear Speckles,' Differentiation, Oct. 2004 (Oct. 2004), 72(8):410-8.

Downes JM et al., 'Biological Analogs. Spectroscopic Characteristics of Mercato- and Disulfide-Copper (II) Coordination in Relation to Type I Proteins,' Inorg Chem, Apr. 1981 (Apr. 1981), 20(4):1081-6.

Díez-Barra E et al., 'Double Michael Addition of Azoles to Methyl Propiolate: A Straightforward Entry to Ligands With Two Heterocyclic Rings,' Tetrahedron Lett, Aug. 7, 2004 (Aug. 7, 2004)(ePub), 45(2004):6937-9.

Elslager et al., "Synthesis of 5,5'[[[3-(dimethylamino)propyl]imino]]bis[3-(trichloromethyl)-1,2,4-thiadiazole] and related thiadiazoles as antimalarial agents." Journal of Heterocyclic Chemistry 1973, 10, 611-622.

Ferrara N and Alitalo K, 'Clinical Applications of Angiogenic Growth Factors and Their Inhibitors,' Nat Med, Dec. 1999 (Dec. 1999), 5(12):1359-64.

Galardon E et al., 'Modeling the Inhibition of Peptide Deformylase by Hydroxamic Acids: Influence of the Sulfur Donor,' Daltron Trans, Mar. 14, 2007 (Mar. 14, 2007) Jan. 23, 2007 (Jan. 23, 2007)(ePub), (10):1047-52.

Giannini G et al., 'Exploring bis-(indolyl)methane Moiety as an Alternative and Innovative CAP Group in the Design of Historic Deacetylase (HDAC) Inhibitors,' Bioorg Med Chem Lett, May 15, 2009 (May 15, 2009) Mar. 26, 2009 (Mar. 26, 2009)(ePub), 19(10):2840-3.

Gillespie J et al., 'Histone Deacetylases are Dysregulated in Rheumatoid Arthritis and a Novel Histone Deacetylase 3-Selective Inhibitor Reduces Interleukin-6 Production by Peripheral Blood Mononuclear Cells from Rheumatoid Arthritis Patients,' Arthritis Rheum, Feb. 2012 (Feb. 2012), 64(2):418-22.

Govindarajan N et al., 'Reducing HDAC6 Ameliorated Cognitive Deficits in Mouse Model for Alzheimer's Disease,' EMBO Mol Med, Jan. 2013 (Jan. 2013) Nov. 26, 2012 (Nov. 26, 2013)(ePub), 5(1):52-63.

Grattagliano I et al., 'Glutathione Peroxidase, Thioredoxin, and Membrane Protein Changes in Erythrocytes Predict Ribavirin-Induced Anemia,' Clin Pharmacol Ther, Oct. 2005 (Oct. 2005), 78(4):422-32.

Gryder BE at al., 'Histone Deacetylase Inhibitors Equipped with Estrogen Receptor Modulation Activity,' J Med Chem, Jul. 25, 2013 (Jul. 25, 2013) Jul. 3, 2013 (Jul. 3, 2013)(ePub), 56(14):5782-96.

Hancock WW et al., 'HDAC Inhibitor Therapy in Autoimmunity and Transplantation,' Ann Rheum Dis, Apr. 2012 (Apr. 2012), 71(Supp 2):i46-54.

Haquette P et al., 'Synthesis of N-Functionalized 2,2'-dipyridylamine Ligands, Complexation to Ruthenium (II) and Anchoring of Complexes to Papain from Papaya Latex,' J Organomet Chem, Mar. 15, 2009 (Mar. 15, 2009), 694(6):937-41.

Hawtree S et al., 'The Role of Histone Deacetylases in Rheumatoid Arthritis Fibroblast-like Synoviocytes,' Biochem Soc Trans, Jun. 2013 (Jun. 2013), 41(3):783-8.

Hayakawa M et al., 'Synthesis and Biological Evaluation cf pyrido[3',2'4,5]furo[3,2-d] Pyrimidine Derivatives as Novel PI3 Kinasae p110alpha inhibitors,' Bioorg Med Chem Lett, May 1, 2007 (May 1, 2007) Feb. 15, 2007 (Feb. 15, 2007)(ePub), 17(9):2438-42.

Hebbel RP et al., 'The HDAC Inhibitors Trichcstatin A and Suberoylanalide Hydroxamic Acid Exhibit Multiple Modalities of Benefit for the Vascular Pathobiology of Sickle Transgenic Mice,' Blood, Mar. 25, 2010 (Mar. 25, 2010) Jan. 6, 2010 (Jan. 6, 2010), 115(12):2483-90.

Imesch P et al., 'Romidepsin Reduces Histone Deacetylase Activity, Induces Acetylation of Histones, Inhibits Proliferation, and Activates Apoptosis in Immortalized Epithelial Endometriotic Cells,' Fertil Steril, Dec. 2010 (Dec. 2010) Jun. 3, 2010 (Jun. 3, 2010)(ePub), 94(7):2838-42.

International Searching Authority, International Preliminary Report on Patentability (Form IB/373) and Written Opinion (Form ISA/

(56) References Cited

OTHER PUBLICATIONS 237) for International Application No. PCT/GB2010/050116 (Form ISA/210), (Beligny S), completed on Apr. 27, 2012 (Apr. 27, 2012) and dated Aug. 2, 2011 (dated Aug. 2, 2011), pp. 1-11.
International Searching Authority, International Preliminary Report on Patentability (Form IB/373) and Written Opinion (Form ISA/237) for International Application No. PCT/GB2010/051370 (Form ISA/210), (Helps I), completed on Oct. 28, 2010 (Oct. 28, 2010) and dated Feb. 21, 2012 (dated Feb. 21, 2012), pp. 1-6.
International Searching Authority, International Preliminary Report on Patentability (Form IB/373) and Written Opinion (Form ISA/237) for International Application No. PCT/GB2011/050824 (Form ISA/210), (Marzi E), completed on Jun. 27, 2011 (Jun. 27, 2011) and dated Nov. 6, 2012 (dated Nov. 6, 2012), pp. 1-7.
International Searching Authority, International Preliminary Report on Patentability (Form IB/373) and Written Opinion (Form ISA/237) for International Application No. PCT/GB2013/050583 (Form ISA/210), (Wolf C), completed on Apr. 11, 2013 (Apr. 11, 2013) and dated Sep. 9, 2014 (dated Sep. 9, 2014), pp. 1-6.
International Searching Authority, International Preliminary Report on Patentability (Form IB/373) and Written Opinion (Form ISA/237) for International Application No. PCT/GB2013/052917 (Form ISA/210), (Sotoca Usina E), completed on Jan. 8, 2014 (Jan. 8, 2014) and dated May 12, 2015 (dated May 12, 2015), pp. 1-11.
International Searching Authority, International Preliminary Report on Patentability (Form IB/373) and Written Opinion (Form ISA/237) for International Application No. PCT/GB2014/051454 (Form ISA/210), (Sotoca Usina E), completed on Jun. 10, 2014 (Jun. 10, 2014) and dated Nov. 10, 2015 (dated Nov. 10, 2015), pp. 1-7.
International Searching Authority, International Search Report for International Application No. PCT/GB2010/050116 (Form ISA/210), (Beligny S), completed on Apr. 27, 2012 (Apr. 27, 2012) and dated May 10, 2010 (dated May 10, 2010), pp. 1-6.
International Searching Authority, International Search Report for International Application No. PCT/GB2010/051370 (Form ISA/210), (Helps I), completed on Oct. 28, 2010 (Oct. 28, 2010) and dated Nov. 9, 2010 (dated Nov. 9, 2010), pp. 1-4.
International Searching Authority, International Search Report for International Application No. PCT/GB2011/050824 (Form ISA/210), (Marzi E), completed on Jun. 27, 2011 (Jun. 27, 2011) and dated Jul. 12, 2011 (dated Jul. 12, 2011), pp. 1-5.
International Searching Authority, International Search Report for International Application No. PCT/GB2013/050583 (Form ISA/210), (Wolf C), completed on Apr. 11, 2013 (Apr. 11, 2013) and dated May 6, 2013 (dated May 6, 2013), pp. 1-4.
International Searching Authority, International Search Report for International Application No. PCT/GB2013/052917 (Form ISA/210), (Sotoca Usina E), completed on Jan. 8, 2014 (Jan. 8, 2014) and dated Jan. 22, 2014 (dated Jan. 22, 2014), pp. 1-9.
International Searching Authority, International Search Report for International Application No. PCT/GB2014/051454 (Form ISA/210), (Sotoca Usina E), completed on Jun. 10, 2014 (Jun. 10, 2014) and dated Jun. 17, 2014 (dated Jun. 17, 2014), pp. 1-4.
International Searching Authority, International Search Report for International Application No. PCT/GB2015/053256 (Form ISA/210), (Ladenburger C), completed on Nov. 26, 2015 (Nov. 26, 2015) and dated Dec. 8, 2015 (dated Dec. 8, 2015), pp. 1-7.
International Searching Authority, International Search Report for International Application No. PCT/GB2015/053260 (Form ISA/210), (Ladenburger C), completed on Nov. 30, 2015 (Nov. 30, 2015) and dated Dec. 9, 2015 (dated Dec. 9, 2015), pp. 1-9.
International Searching Authority, Written Opinion (Form ISA/237) for International Application No. PCT/GB2015/053256 (Form ISA/210), (Ladenburger C), completed on Nov. 26, 2015 (Nov. 26, 2015) and dated Dec. 8, 2015 (dated Dec. 8, 2015), pp. 1-6.
International Searching Authority, Written Opinion (Form ISA/237) for International Application No. PCT/GB2015/053260 (Form ISA/210), (Ladenburger C), completed on Nov. 30, 2015 (Nov. 30, 2015) and dated Dec. 9, 2015 (dated Dec. 9, 2015), pp. 1-7.

Kato K et al., 'Thromboxane Synthetase Inhibitors (TXSI). Design, Synthesis, and Evaluation of Novel Series of Omega-Pyridylalkenoic Acids,' J Med Chem, Mar. 1985 (Mar. 1985), 28(3):287-94.
Kazantsev AG and Thompson LM, 'Therapeutic Application of Histone Deacetylase Inhibitors for Central Nervous System Disorders,' Nat Rev Drug Discov, Oct. 2008 (Oct. 2008), 7(10):854-68.
Kim MG et al., 'The Relationship Between Cisplatin Resistance and Histone Deacetylase Isoform Overexpression in Epithelial Ovarian Cancer Cell Lines,' J Gynecol Oncol, Jul. 2012 (Jul. 2012) Jul. 2, 2012 (Jul. 2, 2012)(ePub), 23(3):182-9.
Kirin SI et al., 'Synthesis and Characterization of CuII Complexes with Amino Acid Substituted di(2-pyridyl)amine Ligands,' Eur J Inorg Chem, Jun. 22, 2007 (Jun. 22, 2007)(ePub), 2007(23):3686-94.
Kovacs J and Mokhir A, 'Nucleic Acid Controlled Catalysts of Carboxylic Esters Hydrolysis,' Bioorg Med Chem Lett, Nov. 1, 2008 (Nov. 1, 2008) Sep. 27, 2008 (Sep. 27, 2008)(ePub), 18(21):5722-4.
Kovalskiy DA and Perevalov VP, 'Synthesis of 7-(3-piperidyl)-[1,6]naphthyridine and 7-(4-pipe-ridyl)[1,6]naphthyridine,' Chem Hetercycl Comp, Nov. 24, 2009 (Nov. 24, 2009)(ePub), 45(9):1053-7 ISSN:0009-3122.
Kuendgen A et al., 'Treatment of Poor-Risk Myelodysplastic Syndromes and Acute Myeloid Leukemia with a Combination of 5-Azacytidine and Valproic Acid,' Clin Epigenetics, Aug. 2011 (Aug. 2011) Apr. 8, 2011 (Apr. 8, 2011)(ePub), 2(2):389-99.
Lee et al., "Synthesis and photophysical properties of five-membered ring π-conjugated materials based on bisthiazol-2-yl-amine and their metal complexation studies." Tertahedron. 2010, 66, 9440-9444.
Lee Su et al., 'In vitro and in vivo Osteogenic Activity of Largazole,' ACS Med Chem Lett, Mar. 10, 2011 (Mar. 10, 2011), 2(3):248-51.
Lemon DD et al., 'Cardiac HDAC6 Catalytic Activity is Induced in Response to Chronic Hypertension,' J Mol Cell Cardiol, Jul. 2011 (Jul. 2011) Apr. 23, 2011 (Apr. 23, 2011)(ePub), 51(1):41-50.
Lu W et al., 'Pd-Catalyzed Selective Addition of Heteroaromatic C—H Bonds to C—C Triple Bonds Under Mild Conditions,' Org Lett, Sep. 21, 2000 (Sep. 21, 2000), 2(19):2927-30.
Mai A et al., 'Identification of two new Synthetic Histone Deacetylase Inhibitors that Modulate Globin Gene Expression in Erythroid Cells from Healthy Donors and Patients with Thalassemia,' Mol Pharamcol, Nov. 2007 (Nov. 2007) Jul. 31, 2007 (Jul. 31, 2007)(ePub), 72(5):1111-23.
McGraw AL, 'Romidepsin for the Treatment of T-cell Lymphomas,' Am J Health Syst Pharm, Jul. 1, 2013 (Jul. 1, 2013), 70(13):1115-22.
McKinsey TA, 'The Biology and Therapeutic Implications of HDACs in the Heart,' Handb Exp Pharmacol, 2011 (2011), 206:57-78.
Meredith EL et al., 'Identification of Orally Available Naphthyridine Protein Kinase D Inhibitors,' J Med Chem, Aug. 12, 2010 (Aug. 12, 2010), 53(15):5400-21.
Moradei O et al., 'Histone Deacetylase Inhibitors in Cancer Therapy: New Compounds and Clinical Update of Benzamide-type Agents,' Curr Top Med Chem, 2008 (2008), 8(10):841-58.
Mull RP et al., 'Antihypertensively Active Amidoximes,' J Am Chem Soc, Jul. 1, 1958 (Jul. 1, 1958), 80(14):3769-72.
Nemenoff R, 'Wound Healing: A Role for HDACs in Inhibition of Fibroblast Prolefiration Through Repression of PDGF Receptor-alpha. Focus on Repression of PDGF-R-alpha After Cellular Injury Involves TNF-alpha Formation of a c-Fos-YY1 Complex, and Negative Regulation by HDAC,' Am J Physiol Cell Physiol, Jun. 1, 2012 (Jun. 1, 2012) Mar. 28, 2012 (Mar. 28, 2012)(ePub), 302(11):C1588-9.
Ohashi A et al., 'Covalent Linking of Coordination-Organized Slipped Cofacial Porphyrin Dimers,' Bull Chem Soc Jpn, Feb. 10, 2004 (Feb. 10, 2004)(ePub), 77(2004):365-74.
Oyamada J and Kitamura T, 'Pt(II)-Catalyzes Hydroarylation Reaction of Alkynes with Pyrroles and Furans,' Tetrahedron, Mar. 14, 2009 (Mar. 14, 2009)(ePub), 65(2009):3842-7.
Patra N et al., 'A Novel Histone Deacetylase (HDAC) Inhibitor MHY219 Induces Apoptosis via Up-Regulation of Androgen Recep-

(56) References Cited

OTHER PUBLICATIONS tor Expression in Human Prostate Cancer Cells,' Biomed Pharmacother, Jun. 2013 (Jun. 2013) Feb. 16, 2013 (Feb. 16, 2013)(ePub), 67(5):407-15.
Peters L et al., 'Synthesis and Transition Metal Complexes of 3,3-bis(1-vinylimidazol-2-yl)propionic Acid, A New N,N,O Ligand Suitable for Copolymerisation,' Inorg Chim Acta, Mar. 12, 2011 (Mar. 12, 2011), 374(2011):392-40.
Peters L et al., 'The New Facial Tripod Ligand 3,3-bis(1-methylimidazol-2-yl)propionic Acid and Carbonyl Complexes Thereof Containing Manganese and Rhenium,' J Organomet Chem, Nov. 25, 2004 (Nov. 25, 2004), 690(2005):2009-16.
Pham TX and Lee J, 'Dietary Regulation of Histone Acetylases and Deacetylases for the Prevention of Metabolic Diseases,' Nutrients, Nov. 28, 2012 (Nov. 28, 2012), 4(12):1868-86.
Piscopo M et al., 'H3 and H3.3 Histone mRNA Amounts and Ratio in Oral Squamous Cell Carcinoma and Leukoplakia,' Oral Dis, Mar. 2006 (Mar. 2006), 12(2):130-6.
Price S and Dyke HJ, 'Histone Deacetylase Inhibitors: An Analysis of Recent Patenting Activity,' Exp Opin Therap Patents, Aug. 7, 2007 (Aug. 7, 2007)(ePub), 17(7):745-65.
Richardson PG et al., 'Preclinical Data and Early Clinical Experience Supporting the Use of Histone Deacetylase Inhibitors in Mulitple Myeloma,' Leuk Res, Jul. 2013 (Jul. 2013) Apr. 9, 2013 (Apr. 9, 2013), 37(7):829-37.
Rotili D et al., 'Non-Cancer Uses of Histone Deacetylase Inhibitors: Effects on Infectious Diseases and beta-Hemoglobinopathies,' Curr Top Med Chem, 2009 (2009), 9(3):272-91.
Safdy ME et al., 'Tryptophan Analogues. 1. Synthesis and Antihypertensive Activity of Positional Isomers,' J Med Chem, Jun. 1982 (Jun. 1982), 25(6):723-30.
Saifuddin M et al., 'Water-Accelerated Cationic ?-(7-endo) Cyclisation: Application to Indole-Based Peri-Annulated Polyheterocycles,' Eur J Org Chem, Sep. 2010 (Sep. 2010) Jul. 20, 2010 (Jul. 20, 2010)(ePub), 2010(26):5108-17.
Shanmugam MK and Sethi G, 'Role of Epigenetics in Inflammation-Associated Diseases,' Subcell Biochem, 2013 (2013), 61:627-57 (PubMed ABSTRACT only).
Singh B et al., 'Novel cAMP PDE III Inhibitors: 1,6-naphthyridin-2(1H)-ones,' J Med Chem, Dec. 25, 1992 (Dec. 25, 1992), 35(26):4858-65.
Singh J et al., 'HDAC Inhibitor SAHA Normalizes the Levels of VLCFAs in Human Skin Fibroblasts from X-ALD Patients and Downregulates the Expression of Proinflammatory Cytokines in Abcd1/2-Silenced Mouse Astrocytes,' J Lipid Res, Nov. 2011 (Nov. 2011) Sep. 4, 2011 (Sep. 4, 2011)(ePub), 52(11):2056-69.
Somei et al. "Boronation-thallation, a new approach to the synthesis of indoles having aryl, and/or a heteroaryl substituent at the 4-position," Chem. Pharm. Bull. 34(9), 3971-3973, (1986).
Su GH et al., 'A Novel Histone Decetylase Inhbitor Identified by High-Throughput Transcriptional Screening of a Compound Library,' Cancer Res, Jun. 15, 2000 (Jun. 15, 2000), 60(12):3137-42.
Suzuki T et al., 'Identification of G Protein-Coupled Receptor 120-Selective Agonists Derived from PPARgamma Agonists,' J Med Chem. Dec. 11, 2008 (Dec. 11, 2008), 51(23):7640-4.
Torrioli M et al., 'Treatment with Valproic Acid Ameliorates ADHD Symptoms in Fragile X Syndrome Boys,' Am J Med Genet A, Jun. 2010 (Jun. 2010), 152A(6):1420-7.

Usui S et al., 'Design, Synthesis, and Biological Activity of Novel PPARgamma Ligands Based on Rosiglitazone and 15d-PGJ2,' Bioorg Med Chem Lett, Mar. 15, 2005 (Mar. 15, 2005), 15(6):1547-51.
Van Damme M et al., 'HDAC Isoenzyme Expression is Deregulated in Chronic Lymphocytic Leukemia B-Cells and has a Complex Prognostic Significance,' Epigenetics, Dec. 1, 2012 (Dec. 1, 2012) Oct. 29, 2012 (Oct. 29, 2012), 7(12):1403-12.
Yamamoto T et al., 'Structure-Activity Relationship Study of 1,4-dihydropyridine Derivatives Blocking N-type Calcium Channels,' Bioorg Med Chem Lett, Feb. 15, 2006 (Feb. 15, 2006) Nov. 23, 2005 (Nov. 23, 2005)(ePub), 16(4):798-802.
Ye J, 'Improving Insulin Sensitivity with HDAC Inhibitor,' Diabetes, Mar. 2013 (Mar. 2013), 62(3):685-7.
Zakeeruddin SM et al., 'Glucose Oxidase Mediation by Soluble and Immobilized Electroactive Detergents,' Biosens Bioelectron, 1996 (1996), 11(3):305-15.
Zhang L et al., 'Inhibition of Histone Deacetylase-Induced Myocardial Repair is Mediated by c-Kit in Infarcted Hearts,' J Biol Chem, Nov. 16, 2012 (Nov. 16, 2012) Sep. 28, 2012 (Sep. 28, 2012)(ePub), 287(47):39338-48.
Lobera et al., "Selective class IIa deacetylase inhibition via a nonchelating zinc-binding group." Nat. Chem. Biol. 2013, 9, 319-325.
Falkenberg et al. Nature Reviews Drug Discovery, vol. 13, 673-691, 2014.
Madsen et al. The effect of various zinc binding groups on inhibition of historic deacetylases 1-11. ChemMedChem Mar. 27, 2014:9(3):614026. Epub Dec. 27, 2013.
Bazzaro et al., "Ubiquitin Proteasome System Stress Underlies Synergistic Killing of Ovarian Cancer Cells by Bortezomib and a Novel HDAC6I Inhibitor," Clinical Cancer Research, 14(22):7340-7347, Nov. 15, 2008.
Hanke et al., "Carfilzomib combined with suberanilohydroxamic acid (SAHA) synergistically promotes endoplasmic reticulum stress in non-small cell lung cancer cell lines," J. Cancer Res. Clin Oncol, 142(3):549-560, Sep. 18, 2015.
Hideshima et al., "Small-molecule inhibition of proteasome and aggresome function induces synergistic antitumor activity in multiple myeloma," PNAS, National Academy of Sciences, US, 102(24):8567-8572, Jun. 14, 2005.
International Searching Authority, International Search Report (Form ISA/210) for International Application No. PCT/GB2017/051619, completed on Jul. 26, 2017 and dated Oct. 18, 2017, pp. 1-9.
International Searching Authority, Written Opinion (Form ISA/237) for International Application No. PCT/GB2017/051619, completed on Jul. 26, 2017 and dated Oct. 18, 2017, pp. 1-16.
Jagannath et al., "Combined proteasome and histone deacetylase inhibition: A promising synergy for patients with relapsed/refractory multiple myeloma," Leukemia Research 34(9):1111-1118, Sep. 1, 2010.
San-Miguel et al., "A Phase IB, Multi-Center, Open-Label Dose-Escalation Study of Oral Panobinostat (LBH589) and I.V. Bortezomib in Patients with Relapsed Multple Myeloma," Internet Citation, Dec. 7, 2009, 4 pages.
Santo et al., "Preclinical activity, pharmacodynamic, and pharmacokinetic properties of a selective HDAC6 inhibitor, ACY-1215, in combination with bortezomib in multiple myeloma," Blood, 119(11):2579-2589, Mar. 15, 2012.
Schafer et al., "Pyridylalanine-Containing Hydroxamic Acids as Selective HDAC6 Inhibitors," ChemMedChem 4:283-290 (2009).
U.S. Appl. No. 16/304,789, Combinations Comprising Histone Deacetylase Inhibitors, filed Nov. 27, 2018, Pending.

POLYHETEROARL HISTONE DEACETYLASE INHIBITORS AND THEIR USE IN THERAPY

CROSS-REFERENCE TO RELATED APPLICATIONS

This application is the national stage of International (PCT) Patent Application Serial No. PCT/GB2015/053256, filed Oct. 29, 2015, which claims the benefit of and priority to Great Britain Patent Application No. 1419264.5, filed Oct. 29, 2014, the contents of each of which are hereby incorporated by reference in their entirety.

FIELD OF THE INVENTION

The present invention relates to novel compounds which are inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

WO2010/086646 discloses compounds which act as inhibitors of HDAC. The heteroaryl capping groups and the zinc-binding groups are joined via an alkylene linker.

Co-pending PCT application number PCT/GB2014/051454 discloses the following compounds which are disclaimed from this application:

4-({[5-(6-Aminopyridin-3-Apyridin-2-yl](pyrazin-2-yl)amino}methyl)-N-hydroxybenzamide having the following structure.

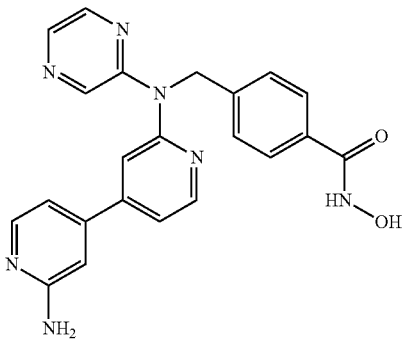 [SMILES: Nc1cc(-c2ccnc(N(Cc3ccc(C(=O)NO)cc3)c3cnccn3)c2)ccn1]

N-hydroxy-4-[({5-[2-(methylamino)pyridin-4-yl]pyridin-2-yl}(pyrazin-2-yl)amino)methyl]benzamide having the following structure.

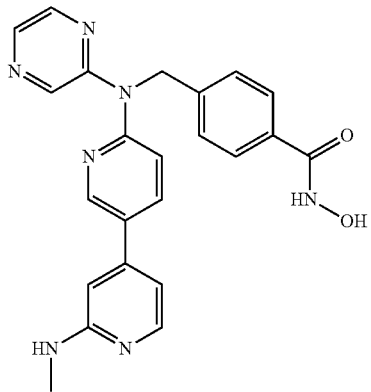 [SMILES: CNc1cc(-c2ccc(N(Cc3ccc(C(=O)NO)cc3)c3cnccn3)nc2)ccn1]

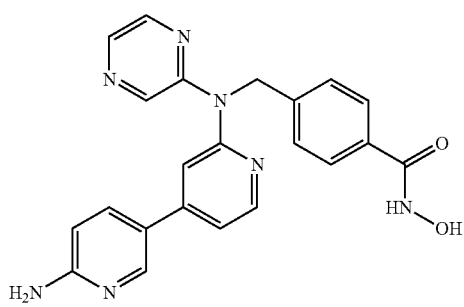

4-({[5-(2-Aminopyridin-4-yl)pyridin-2-yl](pyrazin-2-yl)amino}methyl)-N-hydroxybenzamide having the following structure.

N-hydroxy-4-{[(pyrazin-2-yl)[5-(pyridin-4-yl)pyridin-2-yl]amino]methyl}benzamide having the following structure.

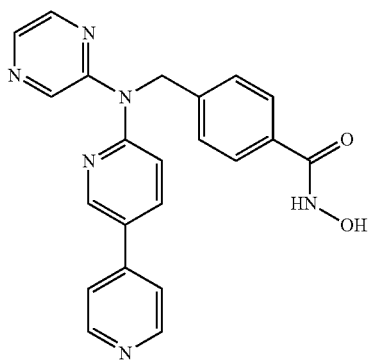 [SMILES: O=C(NO)c1ccc(CN(c2ccc(-c3ccncc3)cn2)c2cnccn2)cc1]

SUMMARY OF THE INVENTION

The present invention is a compound of the formula

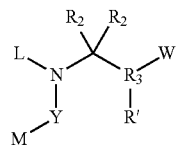

or a pharmaceutically acceptable salt thereof, wherein:

R' is independently selected from H and $QR_1$;

each Q is independently selected from a bond, CO, $CO_2$, NH, S, SO, $SO_2$ or O;

each $R_1$ is independently selected from H, $C_1$-$C_{10}$ alkyl, $C_2$-$C_{10}$ alkenyl, $C_2$-$C_{10}$ alkynyl, aryl, heteroaryl, $C_1$-$C_{10}$ cycloalkyl, halogen, trifluoromethyl, $C_1$-$C_{10}$ alkylaryl, $C_1$-$C_{10}$ alkyl heteroaryl or $C_1$-$C_{10}$ heterocycloalkyl;

L is independently selected from an optionally substituted 6-membered nitrogen-containing heteroaryl;

Y is independently selected from an optionally substituted 6-membered nitrogen-containing heteroaryl;

each M is selected from an optionally substituted 5- to 10-membered heteroaryl;

W is a zinc-binding group, which is not $COOR_1$;

each $R_2$ is independently hydrogen or $C_1$ to $C_6$ alkyl; and $R_3$ is an aryl or heteroaryl;

each aryl or heteroaryl may be substituted by up to three substituents selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl; and each alkyl, alkenyl or alkynyl may be optionally substituted with $C_1$-$C_{10}$ alkyl, $C_2$-$C_{10}$ alkenyl, $C_2$-$C_{10}$ alkynyl, aryl, cycloalkyl, heteroaryl, halogen, $NH_2$, $NO_2$ or hydroxyl, with the proviso that the compound is not 4-({[5-(6-Aminopyridin-3-yl)pyridin-2-yl](pyrazin-2-yl)amino}methyl)-N-hydroxybenzamide;

4-({[5-(2-Aminopyridin-4-yl)pyridin-2-yl](pyrazin-2-yl)amino}methyl)-N-hydroxybenzamide;

N-hydroxy-4-[({5-[2-(methylamino)pyridin-4-yl]pyridin-2-yl}(pyrazin-2-yl)amino)methyl]benzamide; or N-hydroxy-4-{[(pyrazin-2-yl)[5-(pyridin-4-yl)pyridin-2-yl]amino]methyl}benzamide.

In an alternative embodiment, the present invention is a compound represented by:

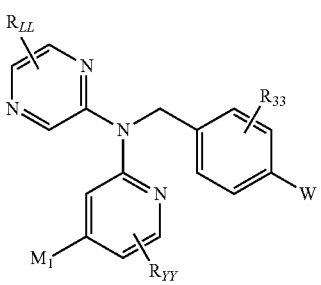

or pharmaceutically acceptable salts thereof, wherein $M_1$ is a 5-6 membered monocyclic heteroaryl or a 8-10 membered bicyclic heteroaryl, preferably a 5-6-membered monocylic heteroaryl, optionally substituted by one, two or three substituents each independently selected from $R^M$;

$R^M$ is selected for each occurrence from the group consisting of $C_{1-6}$alkyl, $C_{2-6}$alkenyl, $C_{2-6}$alkynyl; $C_{1-6}$alkoxy, $C_{3-6}$cycloalkyl, halogen, $NR^aR^b$; —$NR^a$-C(O)—$R^a$; and —$NR^aSO_2$—$R^a$ (wherein $C_{1-6}$alkyl, $C_{2-6}$alkenyl, $C_{2-6}$alkynyl, $C_{1-6}$alkoxy and $C_{3-6}$cycloalkyl may be optionally substituted by one, two or three halogens);

$R_{33}$ is selected from halogen and $C_{1-6}$alkyl (optionally substituted by one, two or three halogens);

W is a zinc binding group;

$R_{LL}$ is selected from the group consisting of H, $CH_3$, and halogen;

$R_{YY}$ is H, $CH_3$, and halogen; and $R^a$ and $R^b$ are each independently selected from H or $C_{1-4}$alkyl; or $R^a$ and $R^b$ taken together with the nitrogen to which they are attached form a 4-6 membered heterocycle.

In a further alternative embodiment, the present invention is a compound represented by:

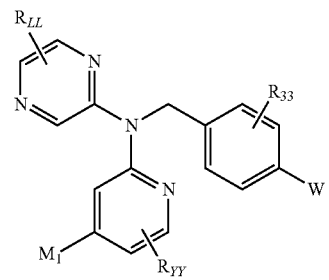

or pharmaceutically acceptable salts thereof, wherein $M_1$ is a 5-membered monocyclic heteroaryl or a 8-10 membered bicyclic heteroaryl, optionally substituted by one, two or three substituents each independently selected from $R^M$;

$R^M$ is selected for each occurrence from the group consisting of $C_{1-6}$alkyl, $C_{2-6}$alkenyl, $C_{2-6}$alkynyl; $C_{1-6}$alkoxy, $C_{3-6}$cycloalkyl, halogen, $NR^aR^b$; —$NR^a$-C(O)—$R^a$; and —$NR^aSO_2$—$R^a$ (wherein $C_{1-6}$alkyl, $C_{2-6}$alkenyl, $C_{2-6}$alkynyl, $C_{1-6}$alkoxy and $C_{3-6}$cycloalkyl may be optionally substituted by one, two or three halogens);

$R_{33}$ is selected for each occurrence from the group consisting of H, halogen and $C_{1-6}$alkyl (optionally substituted by one, two or three halogens);

W is a zinc binding group;

$R_{LL}$ is selected from the group consisting of H, $CH_3$, and halogen;

$R_{YY}$ is H, $CH_3$, and halogen; and $R^a$ and $R^b$ are each independently selected from H or $C_{1-4}$alkyl; or $R^a$ and $R^b$ taken together with the nitrogen to which they are attached form a 4-6 membered heterocycle.

The compounds of the invention may be useful as an inhibitor of HDAC, i.e. in they may be used in a method of treating a disease associated with an over-expression of HDAC.

DESCRIPTION OF THE INVENTION

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, "cycloalkyl" contains from 3 to 10 carbon atoms. It may be monovalent or divalent.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene As used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, heteroaryl means a monocyclic, bicyclic or tricyclic monovalent or divalent (as appropriate) aromatic radical containing at least one and up to four heteroatoms selected from oxygen, nitrogen and sulfur, such as furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Preferred L groups are thiazolyl, imidazolyl, oxazolyl, pyrazolyl, thiadiazolyl and oxadiazolyl.

As used herein, the term "heterocycle" or "heterocycloalkyl" is a mono- or di-valent carbocyclic radical containing up to 4 heteroatoms selected from oxygen, nitrogen and sulfur. It may be monocyclic or bicyclic. It is preferably saturated. The word 'linker' has been used herein to mean di-valent. If the heterocycle is a di-valent linker, the heterocycle may be attached to neighbouring groups through a carbon atom, or through on of the heteroatoms, e.g. a N. Examples of heterocycles are piperazine or morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo e.g. F, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix -ene. This means that the group is divalent, i.e. a linker group.

Preferred Groups of the Invention

The group W is a zinc-chelating residue, i.e. a metallophile capable of binding with zinc in the active site of HDAC. Suitable metallophiles are known to those skilled in the art.

W may be selected from:

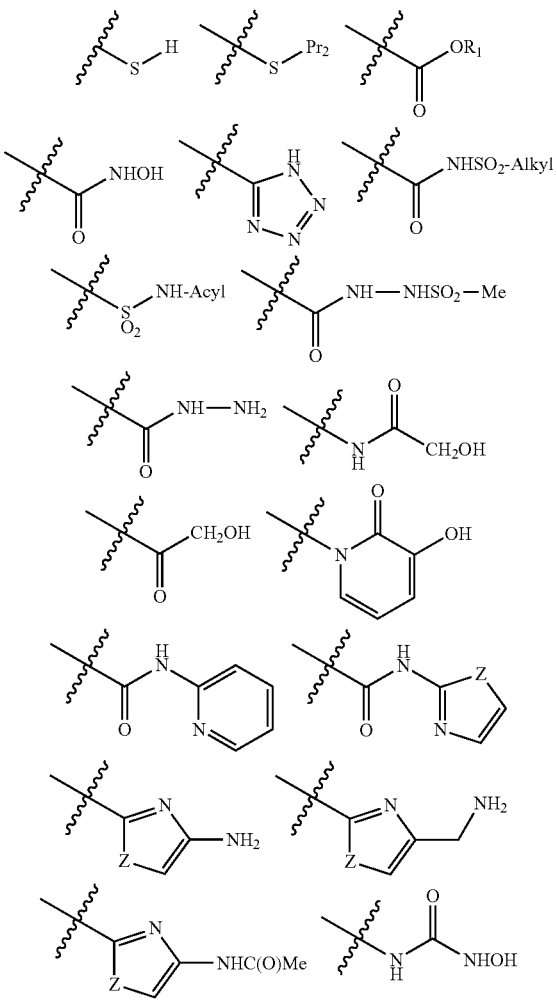

-continued

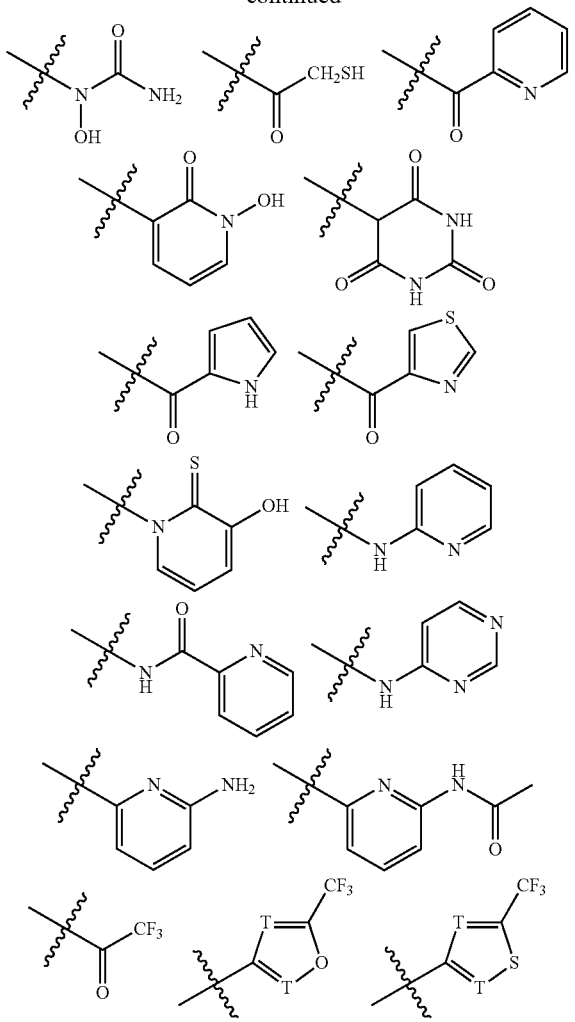

wherein R₁ is as defined in claim 1, Pr² is H or a thiol protecting group, Z is selected from O, S or NH and T is N or CH.

When W is COOR₁, R₁ is not halogen. Preferably, when W is COOR₁, R₁ is H or $C_1$-$C_{10}$ alkyl.

Preferably, W is —COOH, COOMe, —CONHOH, —CONHSO₂CH₃, —CONHNHSO₂CH₃, —CONHNH₂, —CONH(2-pyridyl), —NHCONHOH, tetrazole, hydroxypyridin-2-thione or hydroxypyridin-2-one. Preferably W is not COOR₁. More preferably, W is COOMe, —CONHOH, CONHSO₂CH₃, —CONHNHSO₂CH₃, —CONHNH₂, —CONH(2-pyridyl) —NHCONHOH, tetrazole, hydroxypyridin-2-thione or hydroxypyridin-2-one. Even more preferably, W is —CONHOH, tetrazole, hydroxypyridin-2-thione or hydroxypyridin-2-one Most preferably, W is —CONHOH.

Preferably, L is selected from pyridyl, pyrazinyl, pyrimidinyl and pyridazinyl. More preferably, L is pyrazinyl.

Preferably, L is optionally substituted with H, $C_1$-$C_{10}$ alkyl or O—($C_1$-$C_{10}$ alkyl), halogen, $C_1$-$C_{10}$ heterocycloalkyl, aryl, trifluoromethyl or heteroaryl, more preferably H.

Preferably, Y is selected from pyridyl, pyrazinyl, pyrimidinyl and pyridazinyl. More preferably, Y is pyridyl.

Preferably, M is selected from furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl and oxadiazolyl. More preferably, M is selected from pyrimidinyl, indolyl, pyrazolyl, furanyl, isoxazolyl, pyridyl, azaindolyl. Most preferably, M is pyridyl.

Preferably, M is optionally substituted with H, $C_1$-$C_{10}$ alkyl or O—($C_1$-$C_{10}$ alkyl), halogen, NH₂, $C_1$-$C_{10}$ heterocycloalkyl, aryl, trifluoromethyl, NHC(O)Me, NHSO₂Me or heteroaryl, more preferably H, halogen, NH₂, $C_1$-$C_{10}$ alkyl, NHC(O)Me, NHSO₂Me or trifluoromethyl.

Preferably in at least one, preferably both, of L and Y, the atom that is directly bonded to X is a carbon, and at least one nitrogen atom is directly bonded to said carbon.

Preferably, R₃ is phenylene or phenylene substituted with a halogen. Preferably, wherein the halogen is fluorine.

Preferably, at least one, preferably both, R₂ is/are H.

Preferably, R' is hydrogen or halogen, more preferably hydrogen or fluorine.

In a preferred embodiment, M is:

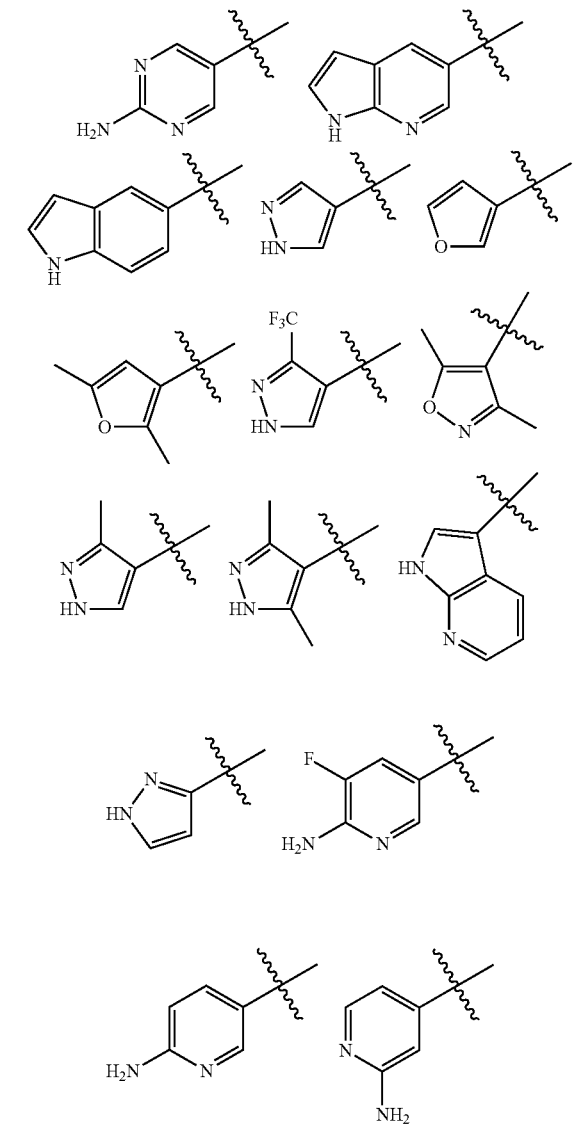

$M_1$ may be represented by:

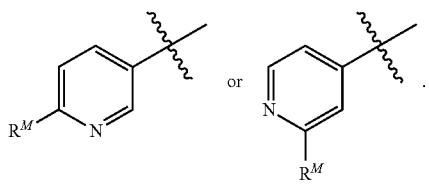

Preferably, $R^M$ may be selected for each occurrence from the group consisting of F, —$CH_3$, $NH_2$, —NH—C(O)—$CH_3$; and —NH—$SO_2$—$CH_3$.

Preferably, the compound of the invention is represented by:

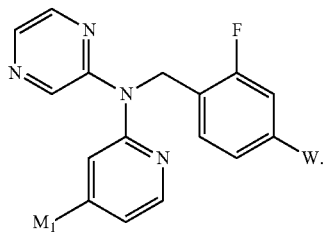

A pharmaceutical composition of the invention comprises a compound as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, ethanedisulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the present invention are found to be inhibitors of HDAC. The compounds of the present invention are therefore therapeutically useful in the treatment of conditions affected by HDAC activity.

The compounds of the invention may be prepared by synthetic routes that will be apparent to those skilled in the art, e.g. based on the Examples.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by co-administration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein.

One set of indications that HDAC inhibitors of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglloneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the HDAC inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of diseases which include some component of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrhythmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *Plasmodium, Cryptosporidium parvum, Toxoplasma gondii, Sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genentically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by S aureus, P acne, candida or aspergillus.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

Compounds of the invention may be tested for HDAC inhibitory activity by any suitable assay, e.g. the assay described in WO2008/062201.

The following Examples illustrate the invention.

Example A 4-({[4-(2-Aminopyrimidin-5-yl)pyridin-2-yl](pyrazin-2-yl)amino}methyl)-N-hydroxybenzamide

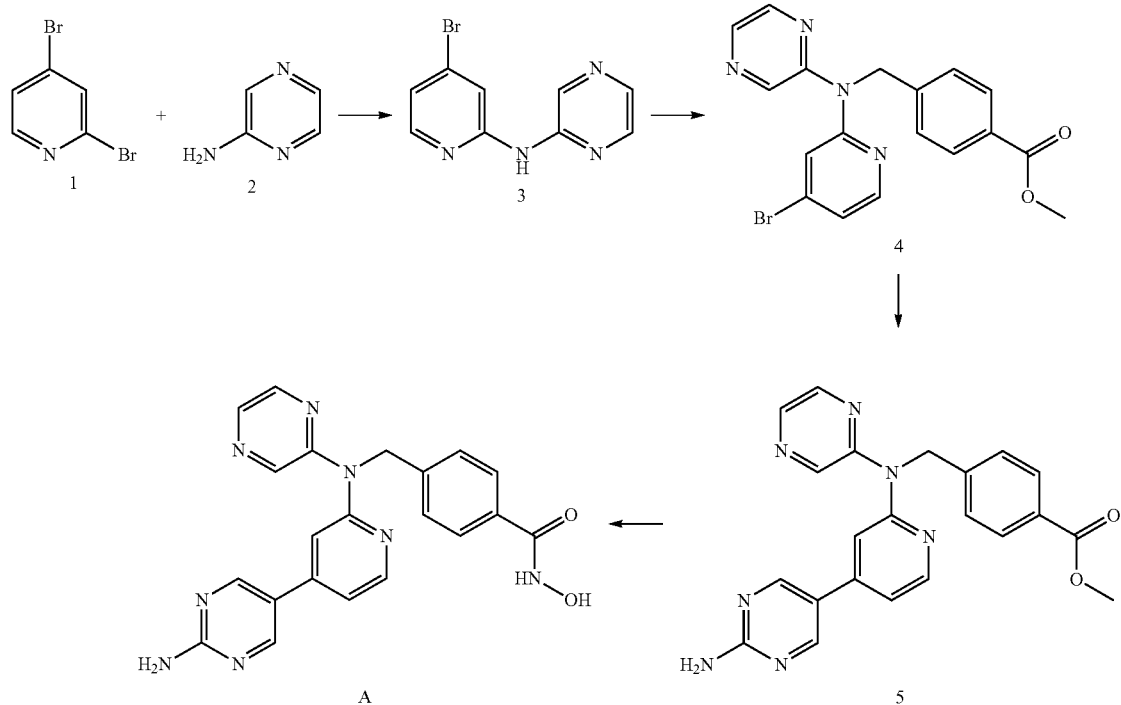

A mixture of 2,4-dibromopyridine (1) (5.0 g, 21.1 mmol), pyrazin-2-amine (2) (2.21 g, 23.2 mmol), Cs$_2$CO$_3$ (15.1 g, 46.4 mmol) and Xantphos (611 mg, 1.05 mmol) was suspended in dioxane (50 mL). The mixture was flushed with N$_2$(g) for 1 min before Pd$_2$(dba)$_3$ (386 mg, 0.42 mmol) was added. Mixture was flushed again with N$_2$(g) and it was heated up to 90° C. overnight. Once cooled, the mixture was partitioned between H$_2$O (150 mL) and EtOAc (3×150 mL). The combined organic extracts were washed with brine, dried with MgSO$_4$, filtered and concentrated in vacuo. Purification by flash column chromatography with heptane/EtOAc (9:1-2:3) yielded (3) (2.6 g, 49%) as pale yellow solid.

$^1$H NMR (500 MHz, Chloroform-d), δ$_H$ ppm: 8.74 (d, J=1.3 Hz, 1H), 8.22 (dd, J=2.6, 1.5 Hz, 1H), 8.15 (d, J=2.7 Hz, 1H), 8.11 (d, J=5.4 Hz, 1H), 8.07 (d, J=1.5 Hz, 1H), 7.63 (s, 1H), 7.10 (dd, J=5.4, 1.6 Hz, 1H).

LCMS (ES): Found 251.0; 253.0 [M+H]$^+$.

To a solution of (3) (1.08 g, 4.3 mmol) in DMF (15 mL) cooled to 0° C. under N$_2$(g) was added NaH (60%, 206 mg, 5.16 mmol). The mixture was stirred for 30 min. Then, a solution of methyl 4-(bromomethyl)benzoate (1.08 g, 4.73 mmol) in DMF (5 mL) was added and the mixture was heated up to 50° C. for 1.5 h. Once cooled down, the reaction was partitioned between H$_2$O (150 mL) and EtOAc (3×150 mL). The combined organic extracts were washed with brine, dried with MgSO$_4$, filtered and concentrated in vacuo. Purification by flash column chromatography with heptane/EtOAc (9:1-2:3) yielded (4) (915 mg, 53%) as white solid.

$^1$H NMR (500 MHz, Chloroform-d), δ$_H$ ppm: 8.66 (d, J=1.4 Hz, 1H), 8.25 (dd, J=2.5, 1.6 Hz, 1H), 8.15 (d, J=5.3 Hz, 1H), 8.13 (d, J=2.6 Hz, 1H), 7.95 (d, J=8.3 Hz, 2H), 7.39 (d, J=8.3 Hz, 2H), 7.33 (d, J=1.4 Hz, 1H), 7.10 (dd, J=5.3, 1.5 Hz, 1H), 5.49 (s, 2H), 3.88 (s, 3H).

LCMS (ES): Found 399.0; 401.0 [M+H]$^+$.

To a suspension of (4) (200 mg, 0.50 mmol), (2-aminopyrimidin-5-yl)boronic acid (84 mg, 0.6 mmol) and Cs$_2$CO$_3$ (326 mg, 1.0 mmol) in DMF (4 mL) and H$_2$O (1 mL) was added Pd(PPh$_3$)$_4$ (58 mg, 0.05 mmol). The reaction mixture was flushed with N$_2$(g) then heated up to 90° C. for 2 h. Once cooled down, H$_2$O (20 mL) was added and the formed precipitate was left to settle at rt for 72 h. Filtration, washings with H$_2$O (2 mL) and drying in vacuo yielded (5) (187 mg, 90%) as a green solid.

$^1$H NMR (500 MHz, Methanol-d$_4$), δ$_H$ ppm: 8.59 (s, 2H), 8.58 (s, 1H), 8.35 (d, J=5.3 Hz, 1H), 8.25-8.29 (m, 1H), 8.04 (d, J=2.5 Hz, 1H), 7.93 (d, J=8.3 Hz, 2H), 7.52 (s, 1H), 7.50 (d, J=8.1 Hz, 2H), 7.33 (d, J=5.3 Hz, 1H), 5.57 (s, 2H), 3.86 (s, 3H).

LCMS (ES): Found 414.5 [M+H]$^+$.

A solution of (5) (187 mg, 0.45 mmol) in 0.85 M NH$_2$OH in MeOH (5 mL) was stirred at rt for 48 h. The volatiles were then removed in vacuo and the residue was purified by reverse prep HPLC to give Example A (6.5 mg, 3%) as an off-white solid.

1H NMR (500 MHz, Methanol-d$_4$), δ$_H$ ppm: 8.58 (s, 2H), 8.56 (d, J=1.4 Hz, 1H), 8.33 (d, J=5.3 Hz, 1H), 8.28 (dd, J=2.6, 1.5 Hz, 1H), 8.03 (d, J=2.7 Hz, 1H), 7.66 (d, J=8.2 Hz, 2H), 7.49 (s, 1H), 7.38 (d, J=8.2 Hz, 2H), 7.31 (dd, J=5.3, 1.4 Hz, 1H), 5.52 (s, 2H).

LCMS (ES): Found 415.2 [M+H]$^+$.

Example B

N-Hydroxy-4-{[(pyrazin-2-yl)(4-{1H-pyrrolo[2,3-b]pyridin-5-yl}pyridin-2-yl)amino]methyl}benzamide

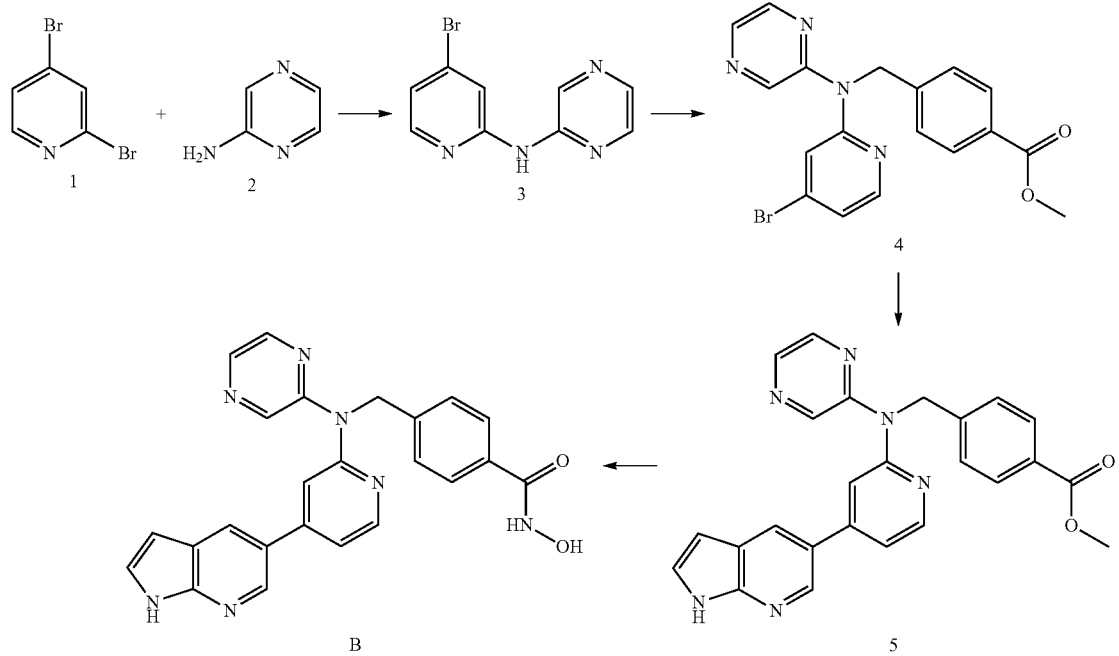

To a suspension of (4) (200 mg, 0.50 mmol), 5-(4,4,5,5-tetramethyl-1,3,2-dioxaborolan-2-yl)-1H-pyrrolo[2,3-b]pyridine (147 mg, 0.6 mmol) and $Cs_2CO_3$ (326 mg, 1.0 mmol) in dioxane (5 mL) and $H_2O$ (2 mL) was added $Pd(PPh_3)_4$ (58 mg, 0.05 mmol). The reaction mixture was flushed with $N_2$(g) then heated up to 90° C. for 2 h. Once cooled down, $H_2O$ (20 mL) was added and the formed precipitate was left to settle at rt for 2 h. Filtration, washings with $H_2O$ (2 mL) and drying in vacuo yielded (5) (230 mg, 72% pure mixed with $Ph_3P=O$) as a brown solid.

$^1$H NMR (500 MHz, DMSO-$d_6$), $\delta_H$ ppm: 11.84 (s, 1H), 8.71 (d, J=1.2 Hz, 1H), 8.59 (d, J=2.1 Hz, 1H), 8.37 (d, J=5.2 Hz, 1H), 8.34 (d, J=2.1 Hz, 1H), 8.27-8.29 (m, 1H), 8.11 (d, J=2.6 Hz, 1H), 7.87 (d, J=8.3 Hz, 2H), 7.71 (s, 1H), 7.54-7.56 (m, 1H), 7.52 (d, J=8.3 Hz, 2H), 7.47-7.49 (m, 1H), 6.53 (dd, J=3.3, 1.7 Hz, 1H), 5.59 (s, 2H), 3.80 (s, 3H).

LCMS (ES): Found 437.5 [M+H]$^+$.

A solution of (5) (115 mg, 0.26 mmol) in 0.85M $NH_2OH$ in MeOH (6 mL) was stirred at rt overnight. The volatiles were then removed in vacuo. The residue was partitioned between $H_2O$ (10 mL) and EtOAc (2×10 mL). The combined organic extracts were washed with brine, dried over $MgSO_4$, filtered and concentrated in vacuo. Purification by reverse prep HPLC yielded Example B (9.4 mg, 8%) as a white solid.

1H NMR (500 MHz, Methanol-$d_4$), $\delta_H$ ppm: 8.59 (d, J=1.3 Hz, 1H), 8.45 (d, J=2.0 Hz, 1H), 8.36 (d, J=5.3 Hz, 1H), 8.25-8.29 (m, 2H), 8.03 (d, J=2.7 Hz, 1H), 7.66 (d, J=8.3 Hz, 2H), 7.58 (s, 1H), 7.50 (d, J=8.2 Hz, 2H), 7.45 (d, J=3.5 Hz, 1H), 7.43 (dd, J=5.3, 1.4 Hz, 1H), 6.57 (d, J=3.5 Hz, 1H), 5.57 (s, 2H).

LCMS (ES): Found 438.2 [M+H]$^+$.

Example C

N-Hydroxy-4-({[4-(1H-indol-5-yl)pyridin-2-yl](pyrazin-2-yl)amino}methyl)benzamide

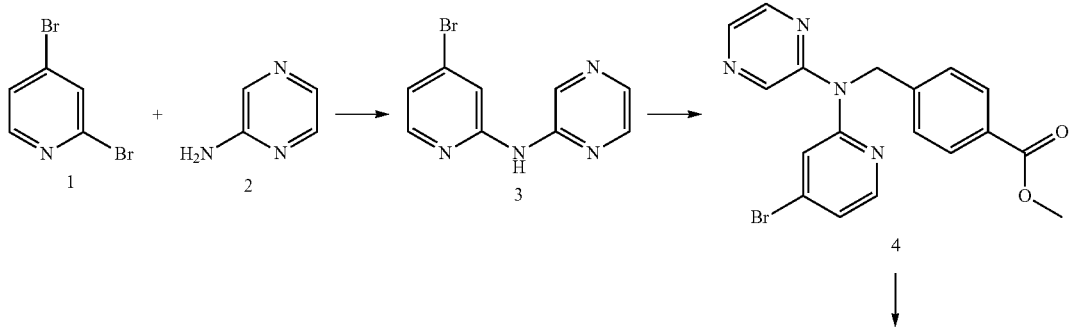

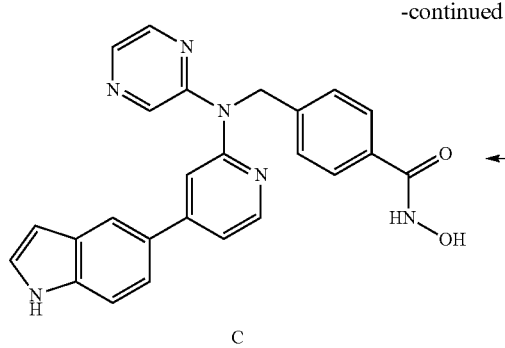

C

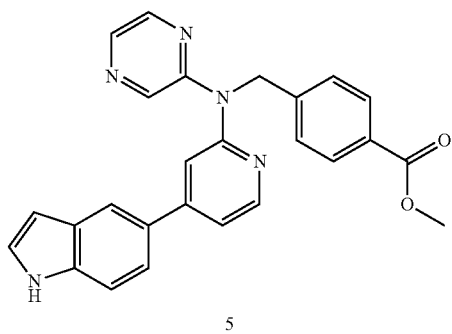

5

To a suspension of (4) (200 mg, 0.50 mmol), 1H-indol-5-ylboronic acid (97 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ then heated up to 90° C. for 2 h. Once cooled down, it was partitioned between $H_2O$ (10 mL) and EtOAc (2×10 mL). The combined organic extracts were washed with brine, dried over $MgSO_4$, filtered and concentrated in vacuo. Purification by flash column chromatography with heptane/EtOAc (4:1-0:1) yielded (5) (196 mg, 90%) as a colourless oil.

$^1$H NMR (500 MHz, Methanol-$d_4$), $\delta_H$ ppm: 8.53 (s, 1H), 8.33 (d, J=5.3 Hz, 1H), 8.26 (d, J=1.2 Hz, 1H), 8.01 (d, J=2.5 Hz, 1H), 7.93 (d, J=8.3 Hz, 2H), 7.88 (s, 1H), 7.57 (s, 1H), 7.51 (d, J=7.9 Hz, 2H), 7.46 (t, J=5.6 Hz, 2H), 7.41 (d, J=8.5 Hz, 1H), 7.29 (d, J=3.0 Hz, 1H), 6.52 (d, J=2.5 Hz, 1H), 5.56 (s, 2H), 3.82-3.87 (m, 3H).

LCMS (ES): Found 436.5 [M+H]$^+$.

A solution of (5) (196 mg, 0.45 mmol) in 0.85M $NH_2OH$ in MeOH (6 mL) was stirred at rt overnight. The volatiles were then removed in vacuo. The residue was purified by reverse prep HPLC to yield Example C (24 mg, 12%) as a white solid.

1H NMR (500 MHz, DMSO-$d_6$), $\delta_H$ ppm: 11.29 (s, 1H), 8.67 (d, J=1.4 Hz, 1H), 8.32 (d, J=5.2 Hz, 1H), 8.27 (dd, J=2.7, 1.5 Hz, 1H), 8.09 (d, J=2.7 Hz, 1H), 7.93-7.97 (m, 1H), 7.61-7.65 (m, 3H), 7.49 (d, J=8.5 Hz, 1H), 7.45 (dd, J=8.5, 1.7 Hz, 1H), 7.41 (dd, J=5.2, 1.5 Hz, 2H), 7.38 (d, J=8.2 Hz, 2H), 6.51 (d, J=2.6 Hz, 1H), 5.52 (s, 2H).

LCMS (ES): Found 437.0 [M+H]$^+$.

Example D

N-Hydroxy-4-{[(pyrazin-2-yl)[4-(1H-pyrazol-4-yl)pyridin-2-yl]amino]methyl}benzamide

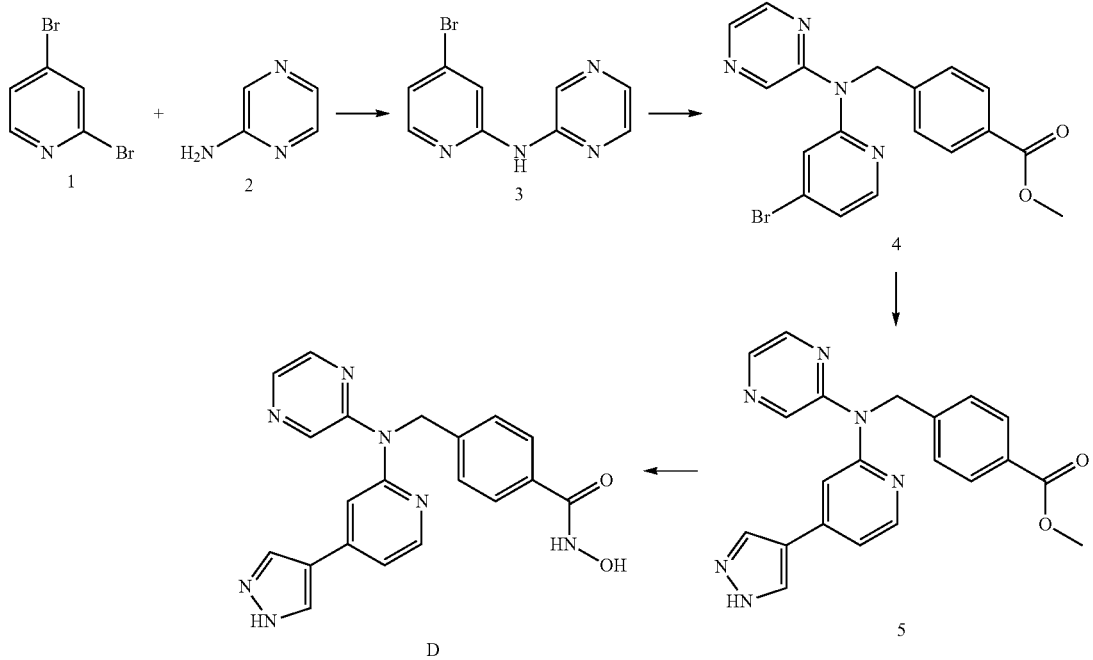

To a suspension of (4) (200 mg, 0.50 mmol), 4-(4,4,5,5-tetramethyl-1,3,2-dioxaborolan-2-yl)-1H-pyrazole (117 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ then heated up to 90° C. for 2 h. Once cooled down, it was partitioned between H₂O (10 mL) and IPA/CHCl₃ (1:2, 4×20 mL). The combined organic extracts were dried over MgSO₄, filtered and concentrated in vacuo. Purification by flash column chromatography with CH₂Cl₂/MeOH (1:0-4:1) yielded (5) (70 mg, 35%) as a yellow gum.

1H NMR (500 MHz, DMSO-d₆), $\delta_H$ ppm: 13.14 (s, 1H), 8.60 (d, J=1.3 Hz, 1H), 8.39 (s, 1H), 8.23-8.26 (m, 2H), 8.08 (d, J=2.6 Hz, 1H), 8.03-8.07 (m, 1H), 7.86 (d, J=8.3 Hz, 2H), 7.58 (s, 1H), 7.49 (d, J=8.3 Hz, 2H), 7.32 (dd, J=5.2, 1.3 Hz, 1H), 5.51 (s, 2H), 3.80 (s, 3H).

LCMS (ES): Found 387.4 [M+H]⁺.

To a solution of (5) (68 mg, 0.18 mmol) in MeOH/THF (1:1, 2 mL) was added NH₂OH (50% in H₂O, 0.22 mL, 3.5 mmol) followed by 6N NaOH (0.06 mL, 0.35 mmol). The reaction mixture was stirred at rt for 40 mins then re-treated with NH₂OH (50% in H₂O, 0.11 mL, 1.8 mmol). After 2.5 h, it was quenched with 1M KHSO₄ (2.5 mL), then partitioned between H₂O (5 mL) and IPA/CHCl₃ (1:2, 5×10 mL). The combined organic extracts were dried over MgSO₄, filtered and concentrated in vacuo. Purification by reverse prep HPLC yielded Example D (2.9 mg, 4%) as an off-white gum.

1H NMR (500 MHz, DMSO-d₆), $\delta_H$ ppm: 13.15 (s, 1H), 11.03 (s, 1H), 8.94 (s, 1H), 8.59 (d, J=1.4 Hz, 1H), 8.17-8.43 (m, 4H), 8.07 (d, J=2.6 Hz, 1H), 7.63 (d, J=8.3 Hz, 2H), 7.59 (s, 1H), 7.41 (d, J=8.3 Hz, 2H), 7.32 (dd, J=5.2, 1.4 Hz, 1H), 5.47 (s, 2H).

LCMS (ES): Found 388.1 [M+H]⁺.

Example E 4-({[4-(Furan-3-yl)pyridin-2-yl](pyrazin-2-yl)amino}methyl)-N-hydroxybenzamide To a suspension of (4) (200 mg, 0.50 mmol), furan-3-ylboronic acid (67.3 mg, 0.6 mmol) and Cs₂CO₃ (163 mg, 0.5 mmol) in DMF (4 mL) and H₂O (1 mL) was added Pd(PPh₃)₄ (58 mg, 0.05 mmol). The reaction mixture was flushed with N₂(g) then it was heated up to 90° C. for 2 h. Once cooled down, it was partitioned between H₂O (10 mL) and IPA/CHCl₃ (1:2, 4×15 mL). The combined organic extracts were dried over MgSO₄, filtered and concentrated in vacuo. Purification by flash column chromatography with heptane/EtOAc (1:0-0:1) yielded (5) (87 mg, 44%) as a brown gum.

1H NMR (500 MHz, DMSO-d₆), $\delta_H$ ppm: 8.62 (s, 1H), 8.41 (s, 1H), 8.29 (d, J=5.2 Hz, 1H), 8.27 (dd, J=2.4, 1.5 Hz, 1H), 8.10 (d, J=2.6 Hz, 1H), 7.86 (d, J=8.3 Hz, 2H), 7.79 (t, J=1.6 Hz, 1H), 7.58 (s, 1H), 7.49 (d, J=8.2 Hz, 2H), 7.32 (d, J=5.2 Hz, 1H), 7.04 (d, J=1.0 Hz, 1H), 5.52 (s, 2H), 3.80 (s, 3H), LCMS (ES): Found 387.2 [M+H]⁺.

To a solution of (5) (87 mg, 0.22 mmol) in MeOH/THF (1:1, 2 mL) was added NH₂OH (50% in H₂O, 0.27 mL, 4.5 mmol) followed by 6N NaOH (0.07 mL, 0.45 mmol). The reaction mixture was stirred at rt for 85 mins. It was quenched with 1M KHSO₄ (2.5 mL), then partitioned between H₂O (5 mL) and IPA/CHCl₃ (1:2, 5×10 mL). The combined organic extracts were dried over MgSO₄, filtered and concentrated in vacuo. Purification by reverse prep HPLC yielded Example E (37 mg, 41%) as an off-white solid.

1H NMR (500 MHz, DMSO-d₆), $\delta_H$ ppm: 11.08 (s, 1H), 8.95 (s, 1H), 8.61 (d, J=1.4 Hz, 1H), 8.41 (s, 1H), 8.29 (d, J=5.2 Hz, 1H), 8.27 (dd, J=2.7, 1.5 Hz, 1H), 8.10 (d, J=2.6 Hz, 1H), 7.79 (t, J=1.7 Hz, 1H), 7.64 (d, J=8.3 Hz, 2H), 7.59 (s, 1H), 7.41 (d, J=8.3 Hz, 2H), 7.32 (dd, J=5.2, 1.4 Hz, 1H), 7.05 (dd, J=1.9, 0.8 Hz, 1H), 5.48 (s, 2H).

LCMS (ES): Found 388.0 [M+H]⁺.

Example F 4-({[4-(2,5-Dimethylfuran-3-yl)pyridin-2-yl](pyrazin-2-yl)amino}methyl)-N-hydroxybenzamide

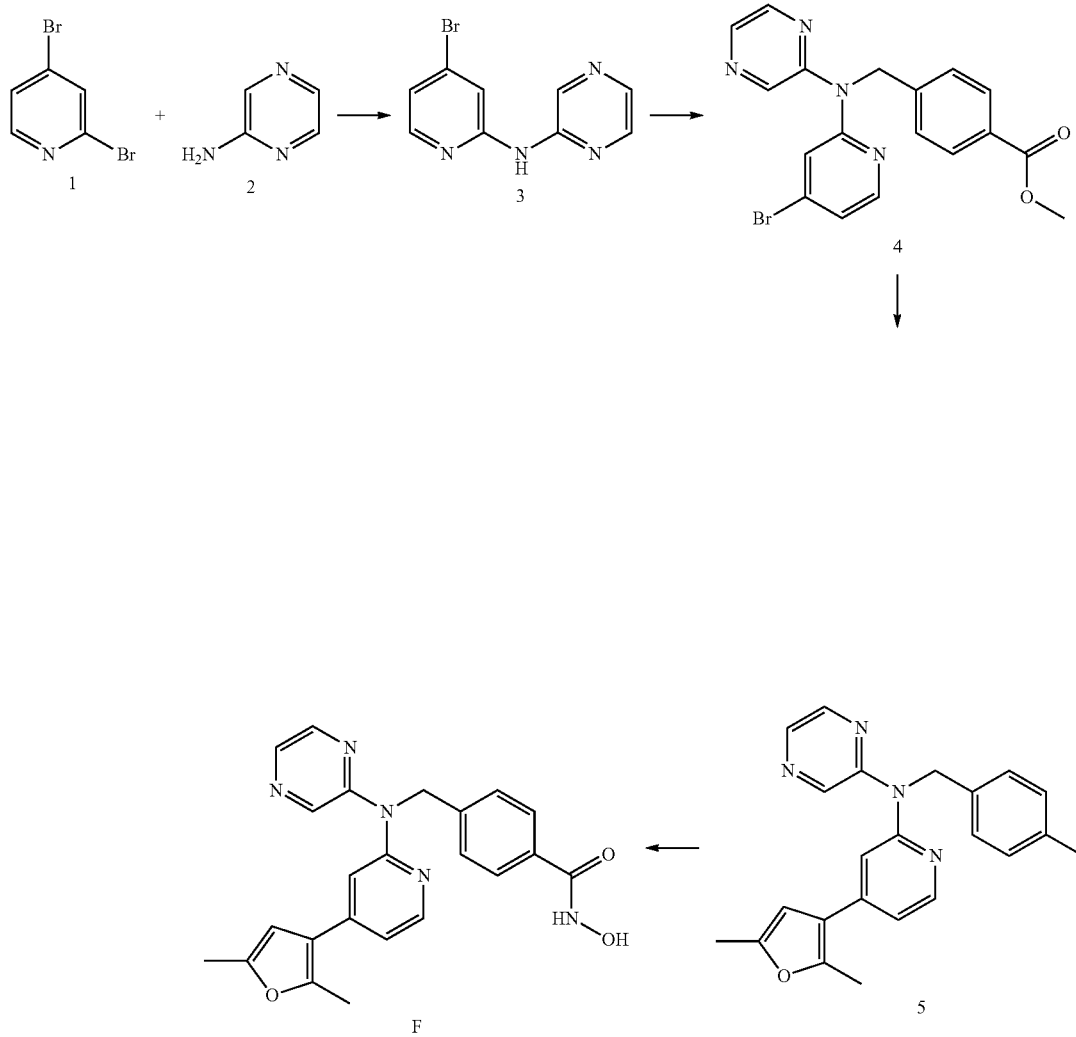

To a suspension of (4) (200 mg, 0.50 mmol), 2-(2,5-dimethylfuran-3-yl)-4,4,5,5-tetramethyl-1,3,2-dioxaborolane (133.5 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ then heated up to 90° C. for 2 h. Once cooled down, it was partitioned between $H_2O$ (10 mL) and IPA/$CHCl_3$ (1:2, 5×10 mL). The combined organic extracts were dried over $MgSO_4$, filtered and concentrated in vacuo. Purification by flash column chromatography with heptane/EtOAc (1:0-0:1) yielded (5) (75 mg, 35%) as an orange solid.

1H NMR (500 MHz, DMSO-$d_6$), $\delta_H$ ppm: 8.69 (d, J=1.2 Hz, 1H), 8.29 (d, J=5.2 Hz, 1H), 8.27 (dd, J=2.5, 1.5 Hz, 1H), 8.11 (d, J=2.6 Hz, 1H), 7.87 (d, J=8.3 Hz, 2H), 7.48 (d, J=8.2 Hz, 2H), 7.27 (s, 1H), 7.11 (dd, J=5.2, 1.2 Hz, 1H), 6.38 (s, 1H), 5.53 (s, 2H), 3.81 (s, 3H), 2.33 (s, 3H), 2.23 (s, 3H).

LCMS (ES): Found 415.2 $[M+H]^+$.

To a solution of (5) (75 mg, 0.18 mmol) in MeOH/THF (1:1, 2 mL) was added $NH_2OH$ (50% in $H_2O$, 0.22 mL, 3.6 mmol) followed by 6N NaOH (0.06 mL, 0.36 mmol). The reaction mixture was stirred at rt for 90 mins. It was then re-treated with $NH_2OH$ (50% in $H_2O$, 0.11 mL, 1.8 mmol) and stirred for another 90 mins. It was quenched with 1M $KHSO_4$ (2.5 mL), then partitioned between $H_2O$ (5 mL) and IPA/$CHCl_3$ (1:2, 5×10 mL). The combined organic extracts were dried over $MgSO_4$, filtered and concentrated in vacuo. Purification by reverse prep HPLC yielded Example F (28 mg, 36%) as an off-white solid.

1H NMR (500 MHz, DMSO-$d_6$), $\delta_H$ ppm: 11.09 (s, 1H), 8.95 (s, 1H), 8.68 (d, J=1.4 Hz, 1H), 8.22-8.33 (m, 2H), 8.10 (d, J=2.6 Hz, 1H), 7.64 (d, J=8.3 Hz, 2H), 7.40 (d, J=8.3 Hz, 2H), 7.28 (s, 1H), 7.10 (dd, J=5.3, 1.4 Hz, 1H), 6.38 (s, 1H), 5.49 (s, 2H), 2.34 (s, 3H), 2.24 (s, 3H).

LCMS (ES): Found 416.3 $[M+H]^+$.

Example G

N-Hydroxy-4-{[(pyrazin-2-yl)({4-[3-(trifluoromethyl)-1H-pyrazol-4-yl]pyridin-2-yl})amino]methyl}benzamide

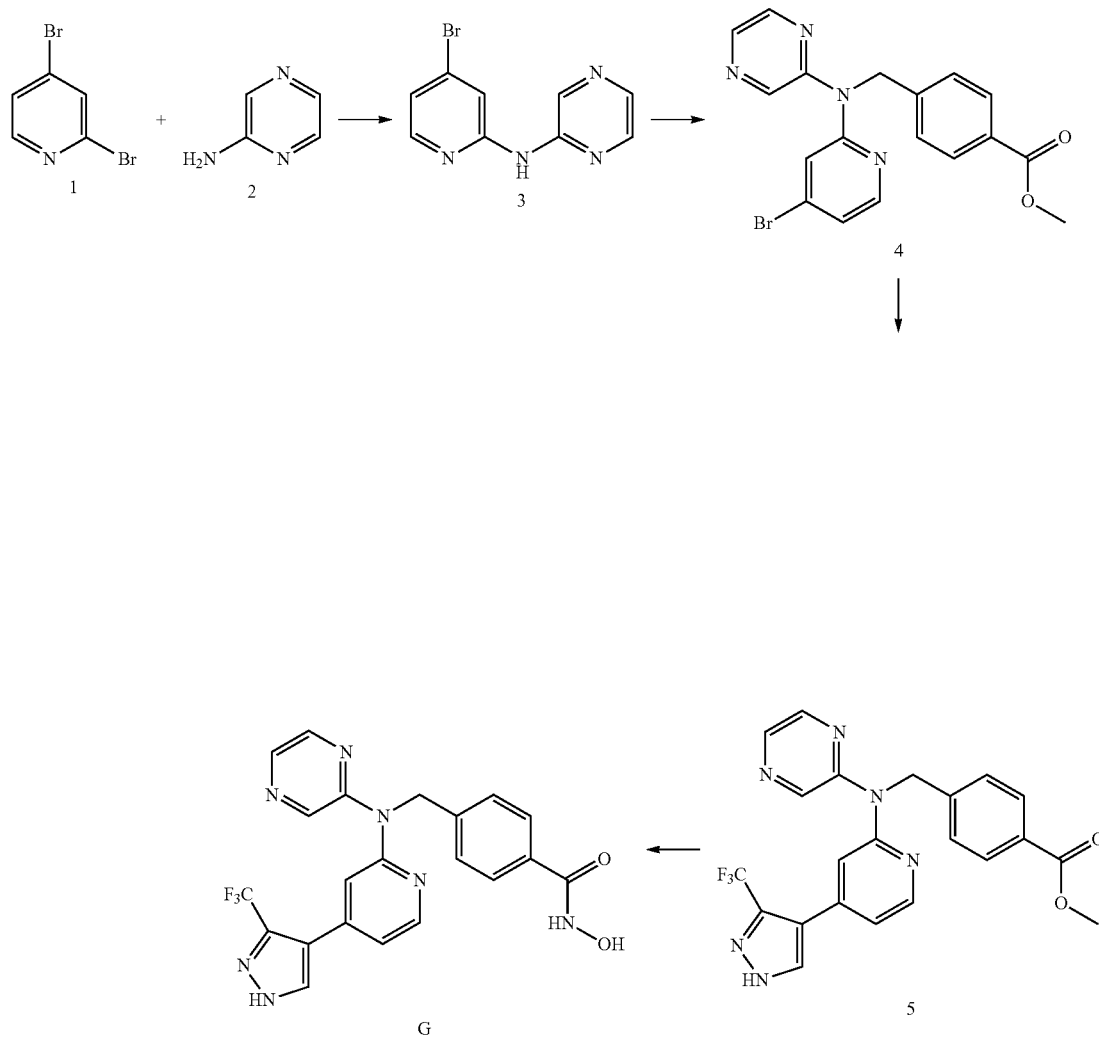

To a suspension of (4) (200 mg, 0.50 mmol), [3-(trifluoromethyl)-1H-pyrazol-4-yl]boronic acid (108.1 mg, 0.6 mmol) and $Cs_2CO_3$ (163 mg, 0.5 mmol) in DMF (4 mL) and $H_2O$ (1 mL) was added $Pd(PPh_3)_4$ (58 mg, 0.05 mmol). The reaction mixture was flushed with $N_2(g)$ then heated up to 90° C. for 2 h. Once cooled down, it was partitioned between $H_2O$ (10 mL) and $IPA/CHCl_3$ (1:2, 4×15 mL). The combined organic extracts were dried over $MgSO_4$, filtered and concentrated in vacuo. Purification by flash column chromatography with heptane/EtOAc (1:0-0:1) yielded (5) (62 mg, 21%) as a yellow gum.

1H NMR (500 MHz, DMSO-$d_6$), $\delta_H$ ppm: 13.94 (s, 1H), 8.69 (d, J=1.4 Hz, 1H), 8.41 (s, 1H), 8.35 (d, J=5.2 Hz, 1H), 8.28 (dd, J=2.6, 1.5 Hz, 1H), 8.14 (d, J=2.6 Hz, 1H), 7.87 (d, J=8.3 Hz, 2H), 7.46 (d, J=8.3 Hz, 2H), 7.34 (s, 1H), 7.14 (dd, J=5.2, 1.2 Hz, 1H), 5.52 (s, 2H), 3.81 (s, 3H).

LCMS (ES): Found 455.1 [M+H]⁺.

To a solution of (5) (59 mg, 0.13 mmol) in MeOH/THF (1:1, 2 mL) was added $NH_2OH$ (50% in $H_2O$, 0.16 mL, 2.6 mmol) followed by 6N NaOH (0.04 mL, 0.26 mmol). The reaction mixture was stirred at rt for 75 mins. It was then re-treated with $NH_2OH$ (50% in $H_2O$, 0.08 mL, 1.3 mmol), then again after 5 h and stirred for another 90 mins. It was quenched with 1M $KHSO_4$ (2.5 mL), then partitioned between $H_2O$ (5 mL) and $IPA/CHCl_3$ (1:2, 5×10 mL). The combined organic extracts were dried over $MgSO_4$, filtered and concentrated in vacuo. Purification by reverse prep HPLC yielded Example G (9.6 mg, 16%) as a yellow solid.

1H NMR (500 MHz, DMSO-$d_6$), $\delta_H$ ppm: 13.94 (s, 1H), 11.09 (s, 1H), 8.95 (s, 1H), 8.62-8.72 (m, 1H), 8.37-8.44 (m, 1H), 8.35 (d, J=5.3 Hz, 1H), 8.26-8.31 (m, 1H), 8.11-8.15 (m, 1H), 7.55-7.67 (m, 2H), 7.30-7.41 (m, 3H), 7.11-7.16 (m, 1H), 5.43-5.50 (m, 2H).

LCMS (ES): Found 456.2 [M+H]⁺.

Example H 4-({[4-(Dimethyl-1,2-oxazol-4-yl)pyridin-2-yl](pyrazin-2-yl)amino}methyl)-N-hydroxybenzamide

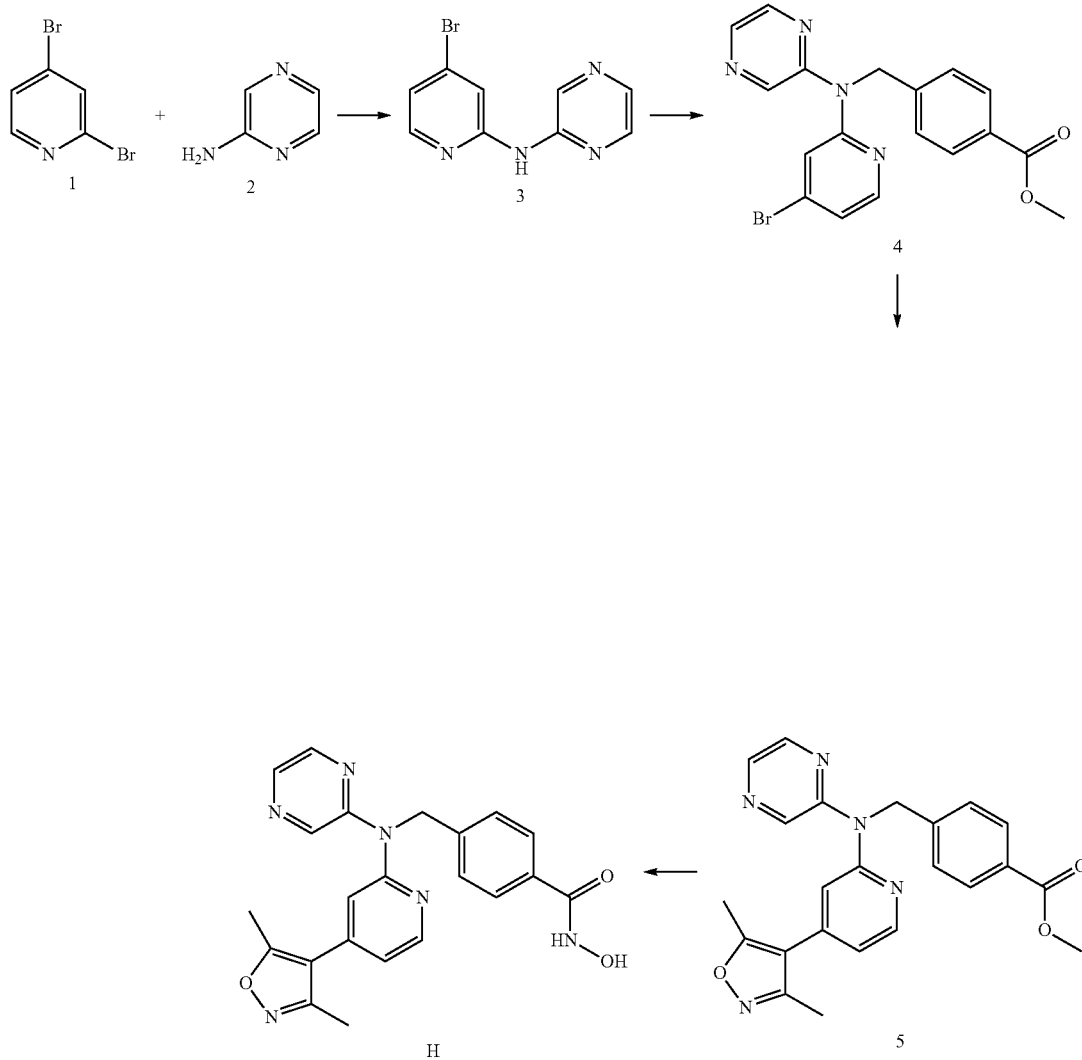

To a suspension of (4) (200 mg, 0.50 mmol), 3,5-dimethyl-4-(tetramethyl-1,3,2-dioxaborolan-2-yl)-1,2-oxazole (112 mg, 0.5 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ then heated up to 90° C. for 2 h. Once cooled down, it was partitioned between $H_2O$ (15 mL) and $CH_2Cl_2$ (3×30 mL). The combined organic extracts were dried over $MgSO_4$, filtered and concentrated in vacuo. Purification by flash column chromatography with $CH_2Cl_2$/MeOH (1:0-19:1) yielded (5) (40 mg, 18%) as a pale yellow solid.

1H NMR (500 MHz, DMSO-$d_6$), $\delta_H$ ppm: 8.69 (d, J=1.5 Hz, 1H), 8.24-8.29 (m, 2H), 8.10 (d, J=2.7 Hz, 1H), 7.87 (d, J=8.3 Hz, 2H), 7.60 (s, 1H), 7.48 (d, J=8.4 Hz, 2H), 7.34 (s, 1H), 7.19 (d, J=4.4 Hz, 1H), 5.98 (br. s., 1H), 5.52 (s, 2H), 3.81 (s, 3H), 2.52 (m, 6H).

LCMS (ES): Found 416.5 $[M+H]^+$.

To a solution of (5) (30 mg, 0.07 mmol) in MeOH/THF (1:1, 2 mL) was added $NH_2OH$ (50% in $H_2O$, 0.09 mL, 1.4 mmol) followed by 6N NaOH (0.02 mL, 0.14 mmol). The reaction mixture was stirred at rt for 1 h. It was then quenched with 1M $KHSO_4$ (2 mL) and partitioned between $H_2O$ (5 mL) and $CH_2Cl_2$ (2×20 mL). The combined organic extracts were dried over $MgSO_4$, filtered and concentrated in vacuo. Purification by reverse prep HPLC yielded Example H (8.8 mg, 16%) as an orange crystalline solid.

1H NMR (500 MHz, DMSO-$d_6$), $\delta_H$ ppm: 8.73 (d, J=3.3 Hz, 1H), 8.38 (d, J=5.2 Hz, 1H), 8.29 (s, 1H), 8.13 (dd, J=5.3, 2.6 Hz, 1H), 7.65 (d, J=8.3 Hz, 1H), 7.58 (d, J=8.3 Hz, 1H), 7.40 (d, J=8.3 Hz, 1H), 7.35 (d, J=8.4 Hz, 1H), 7.29 (d, J=8.0 Hz, 1H), 7.10 (t, J=5.5 Hz, 1H), 5.49 (m, 2H), 2.38 (d, J=1.7 Hz, 3H), 2.20 (s, 3H).

LCMS (ES): Found 417.3 $[M+H]^+$.

Example I

N-Hydroxy-4-({[4-(3-methyl-1H-pyrazol-4-yl)pyridin-2-yl](pyrazin-2-yl)amino}methyl)benzamide

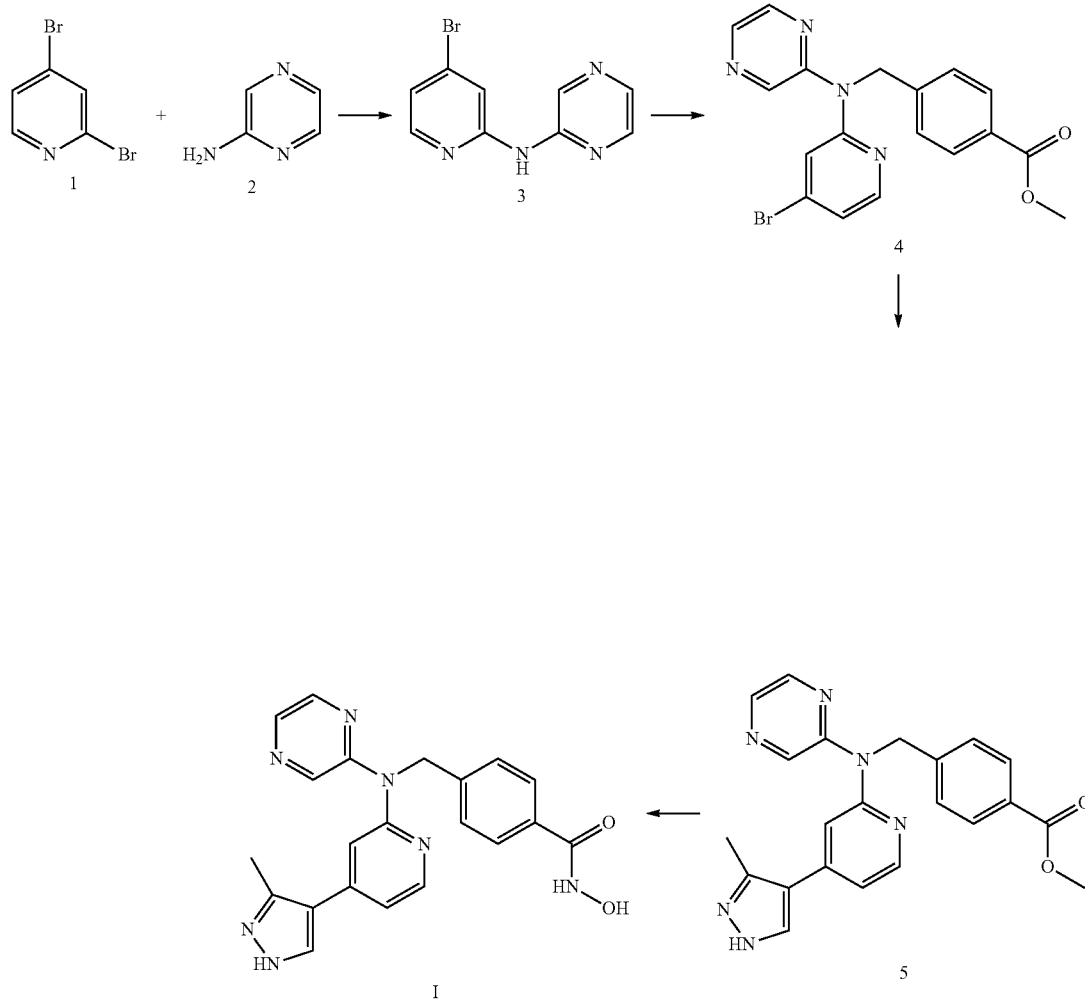

To a suspension of (4) (200 mg, 0.50 mmol), 3-methyl-4-(tetramethyl-1,3,2-dioxaborolan-2-yl)-1H-pyrazole (104 mg, 0.5 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ and heated up to 90° C. for 2 h. It was then re-treated with 3-methyl-4-(tetramethyl-1,3,2-dioxaborolan-2-yl)-1H-pyrazole (104 mg, 0.5 mmol), $Cs_2CO_3$ (326 mg, 1.0 mmol) and $Pd(PPh_3)_4$ (58 mg, 0.05 mmol). The reaction mixture was flushed with $N_2(g)$ and heated up to 90° C. for another 2 h. Once cooled down, it was partitioned between $H_2O$ (10 mL) and $CH_2Cl_2$ (2×30 mL). The combined organic extracts were dried over $MgSO_4$, filtered and concentrated in vacuo. Purification by flash column chromatography with $CH_2Cl_2$/MeOH (1:0-4:1) yielded (5) (67 mg, 33%).

1H NMR (500 MHz, DMSO-$d_6$), $\delta_H$ ppm: 8.69 (d, J=1.5 Hz, 1H), 8.24-8.29 (m, 2H), 8.10 (d, J=2.7 Hz, 1H), 7.87 (d, J=8.3 Hz, 2H), 7.60 (s, 1H), 7.48 (d, J=8.4 Hz, 2H), 7.34 (s, 1H), 7.19 (m, 1H), 5.98 (br. s., 1H), 5.52 (s, 2H), 3.81 (s, 3H), 2.30 (s, 3H).

LCMS (ES): Found 401.5 [M+H]$^+$.

To a solution of (5) (67 mg, 0.17 mmol) in DMSO (2 mL) was added $NH_2OH$ (50% in $H_2O$, 0.21 mL, 3.4 mmol) followed by 6N NaOH (0.06 mL, 0.34 mmol). The reaction mixture was stirred at rt for 4 h. It was then quenched with 1M $KHSO_4$ (2 mL) and partitioned between $H_2O$ (5 mL) and $CH_2Cl_2$ (2×20 mL). The combined organic extracts were dried over $MgSO_4$, filtered and concentrated in vacuo. Purification by reverse prep HPLC yielded Example I (3.7 mg, 5%) as an orange crystalline solid.

1H NMR (500 MHz, DMSO-$d_6$), $\delta_H$ ppm: 12.84 (br. s., 1H), 11.04 (br. s., 1H), 8.96 (br. s., 1H), 8.65-8.70 (m, 1H), 8.23-8.30 (m, 2H), 8.09 (dd, J=5.6, 2.6 Hz, 1H), 7.94 (s, 1H), 7.65 (d, J=8.2 Hz, 1H), 7.58 (d, J=8.2 Hz, 1H), 7.40 (d, J=8.2 Hz, 1H), 7.27-7.37 (m, 2H), 7.15-7.21 (m, 1H), 5.47 (m, 2H), 2.30 (m, 3H).

LCMS (ES): Found 402.2 [M+H]$^+$.

Example J 4-({[4-(3,5-Dimethyl-1H-pyrazol-4-yl)pyridin-2-yl](pyrazin-2-yl)amino}methyl)-N-hydroxybenzamide

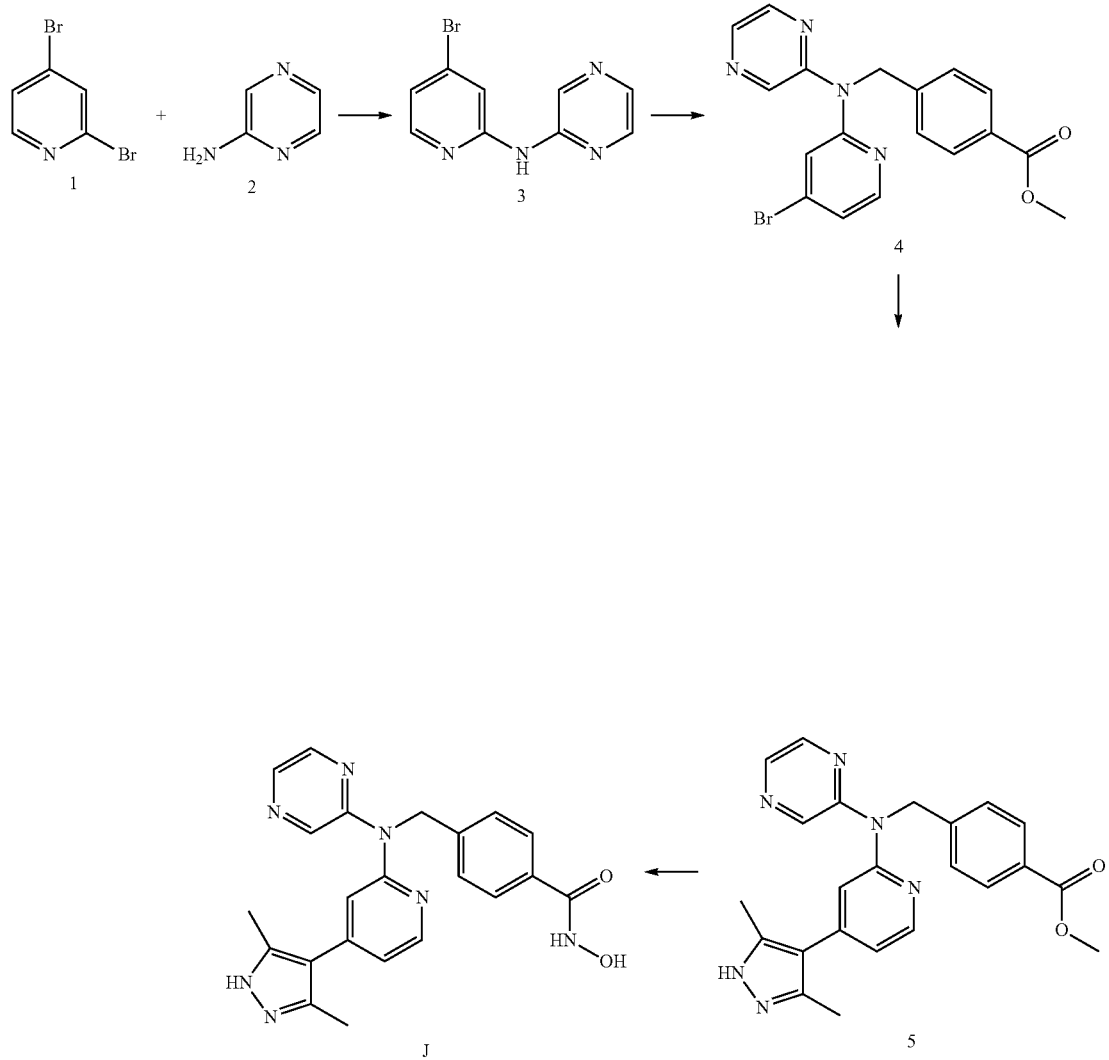

To a suspension of (4) (200 mg, 0.50 mmol), 3,5-dimethyl-4-(tetramethyl-1,3,2-dioxaborolan-2-yl)-1H-pyrazole (134 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The reaction mixture was flushed with $N_2(g)$ and heated up to 90° C. for 2 h. It was then re-treated with $Pd(PPh_3)_4$ (58 mg, 0.05 mmol). The reaction mixture was flushed with $N_2(g)$ and heated up to 90° C. for another 1 h. Once cooled down, it was partitioned between $H_2O$ (15 mL) and $IPA/CHCl_3$ (1:2, 3×30 mL). The combined organic extracts were dried over $MgSO_4$, filtered and concentrated in vacuo. Purification by prep HPLC yielded (5) (85 mg, 39%).

1H NMR (500 MHz, DMSO-$d_6$), $\delta_H$ ppm: 12.46 (br. s., 1H), 8.72 (d, J=1.3 Hz, 1H), 8.30 (d, J=5.2 Hz, 1H), 8.25-8.27 (m, 1H), 8.10 (d, J=2.6 Hz, 1H), 7.88 (d, J=8.3 Hz, 2H), 7.48 (d, J=8.3 Hz, 2H), 7.13 (s, 1H), 7.03 (dd, J=5.2, 1.2 Hz, 1H), 5.52 (s, 2H), 3.81 (s, 3H), 2.16 (s, 6H).

LCMS (ES): Found 415.4 [M+H]$^+$.

To a solution of (5) (85 mg, 0.21 mmol) in MeOH/THF (1:1, 1 mL) was added $NH_2OH$ (50% in $H_2O$, 0.25 mL, 4.1 mmol) followed by 6N NaOH (0.07 mL, 0.34 mmol). The reaction mixture was stirred at rt for 1 h. It was then quenched with 1M $KHSO_4$ (2 mL) and $H_2O$ (5 mL). A precipitate formed, it was filtered, washed with $H_2O$ (2×5 mL) and dried in vacuo to yield Example J (54.9 mg, 62%) as an off-white solid.

1H NMR (500 MHz, DMSO-$d_6$), $\delta_H$ ppm: 12.47 (br. s., 1H), 11.10 (br. s., 1H), 8.95 (br. s., 1H), 8.71 (d, J=1.3 Hz, 1H), 8.30 (d, J=5.2 Hz, 1H), 8.26 (dd, J=2.5, 1.5 Hz, 1H), 8.10 (d, J=2.6 Hz, 1H), 7.65 (d, J=8.3 Hz, 2H), 7.39 (d, J=8.2 Hz, 2H), 7.14 (s, 1H), 7.03 (dd, J=5.2, 1.2 Hz, 1H), 5.48 (s, 2H), 2.16 (s, 6H).

LCMS (ES): Found 416.4 [M+H]$^+$.

Example K

N-Hydroxy-4-{[(pyrazin-2-yl)(4-{1H-pyrrolo[2,3-b]pyridin-3-yl}pyridin-2-yl)amino]methyl}benzamide

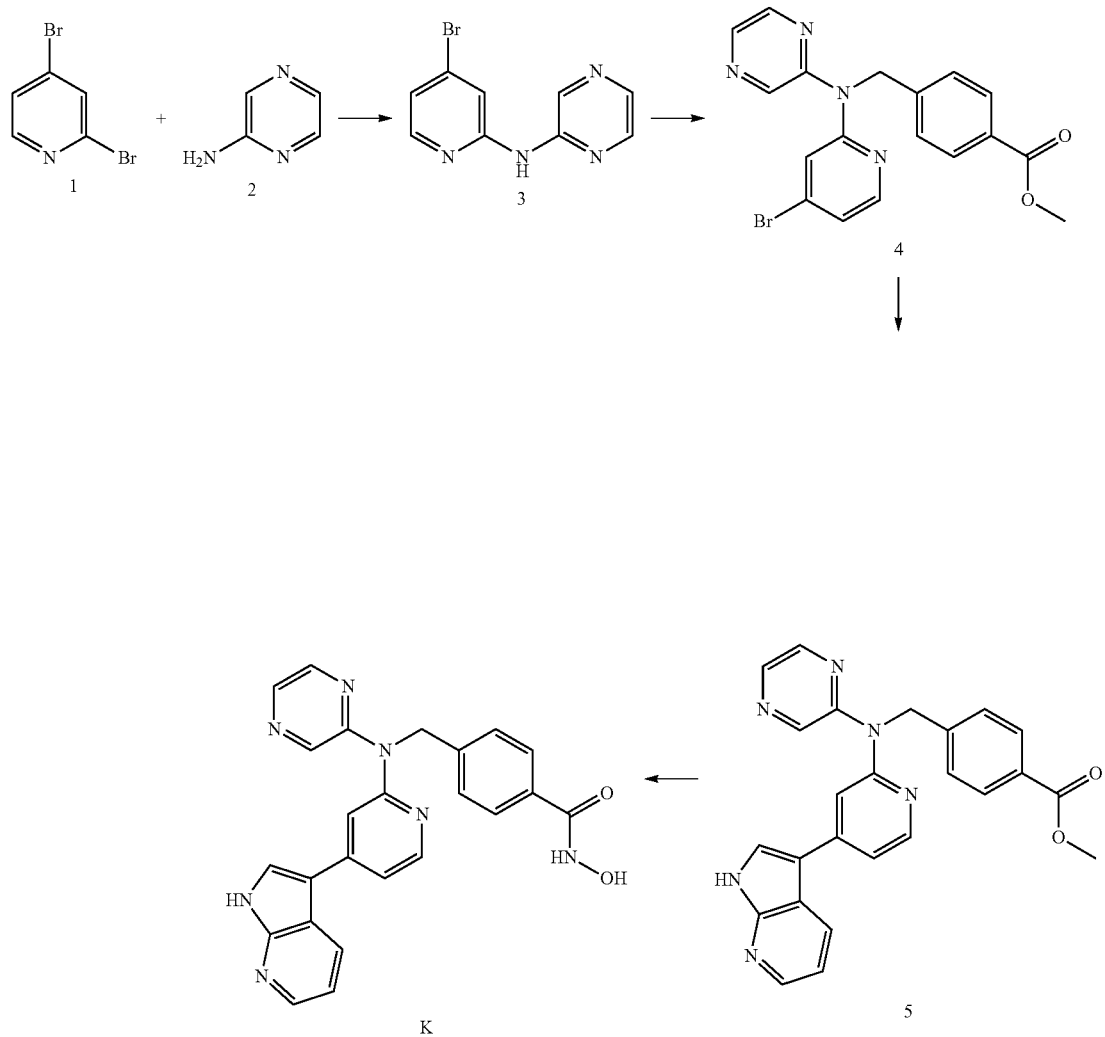

To a suspension of (4) (200 mg, 0.50 mmol), 3-(tetramethyl-1,3,2-dioxaborolan-2-yl)-1H-pyrrolo[2,3-b]pyridine (147 mg, 0.6 mmol) and Cs$_2$CO$_3$ (326 mg, 1.0 mmol) in DMF (4 mL) and H$_2$O (1 mL) was added Pd(PPh$_3$)$_4$ (58 mg, 0.05 mmol). The reaction mixture was flushed with N$_2$(g) and heated up to 90° C. for 2 h. It was then re-treated with Pd(PPh$_3$)$_4$ (58 mg, 0.05 mmol). The reaction mixture was flushed with N$_2$(g) and heated up to 90° C. for another 1 h. Once cooled down, it was partitioned between H$_2$O (15 mL) and IPA/CHCl$_3$ (1:2, 3×30 mL). The combined organic extracts were dried over MgSO$_4$, filtered and concentrated in vacuo. Purification by flash column chromatography with CH$_2$Cl$_2$/MeOH (1:0-9:1) yielded (5) (168 mg, 65%) as an orange solid.

1H NMR (500 MHz, DMSO-d$_6$), $\delta_H$ ppm: 12.20 (s, 1H), 8.73 (s, 1H), 8.27-8.33 (m, 3H), 8.17 (s, 1H), 8.07-8.14 (m, 2H), 7.90 (d, J=8.3 Hz, 2H), 7.60 (s, 1H), 7.53 (d, J=8.2 Hz, 2H), 7.46 (d, J=6.3 Hz, 1H), 7.13 (dd, J=8.0, 4.7 Hz, 1H), 5.57 (s, 2H), 3.81 (s, 3H).

LCMS (ES): Found 437.0 [M+H]$^+$.

To a solution of (5) (84 mg, 0.19 mmol) in MeOH/THF (1:1, 1 mL) was added NH$_2$OH (50% in H$_2$O, 0.24 mL, 3.9 mmol) followed by 6N NaOH (0.06 mL, 0.39 mmol). The reaction mixture was stirred at rt for 1 h. It was then quenched with 1M KHSO$_4$ (2 mL) and H$_2$O (5 mL). A precipitate formed, it was filtered, washed with H$_2$O (2×5 mL) and dried in vacuo. It was subsequently purified by reverse prep HPLC to yield Example K (20.0 mg, 24%) as an off-white solid.

1H NMR (500 MHz, DMSO-d$_6$), $\delta_H$ ppm: 12.20 (br. s., 1H), 11.11 (br. s., 1H), 8.96 (br. s., 1H), 8.73 (d, J=1.3 Hz, 1H), 8.27-8.32 (m, 3H), 8.17 (s, 1H), 8.11 (d, J=2.7 Hz, 1H), 8.06 (d, J=8.1 Hz, 1H), 7.67 (d, J=8.2 Hz, 2H), 7.59 (s, 1H), 7.42-7.47 (m, 3H), 7.14 (dd, J=8.0, 4.6 Hz, 1H), 5.53 (s, 2H).

LCMS (ES): Found 438.2 [M+H]$^+$.

Example L

N-Hydroxy-4-{[(pyrazin-2-yl)[4-(1H-pyrazol-3-yl)pyridin-2-yl]amino]methyl}benzamide

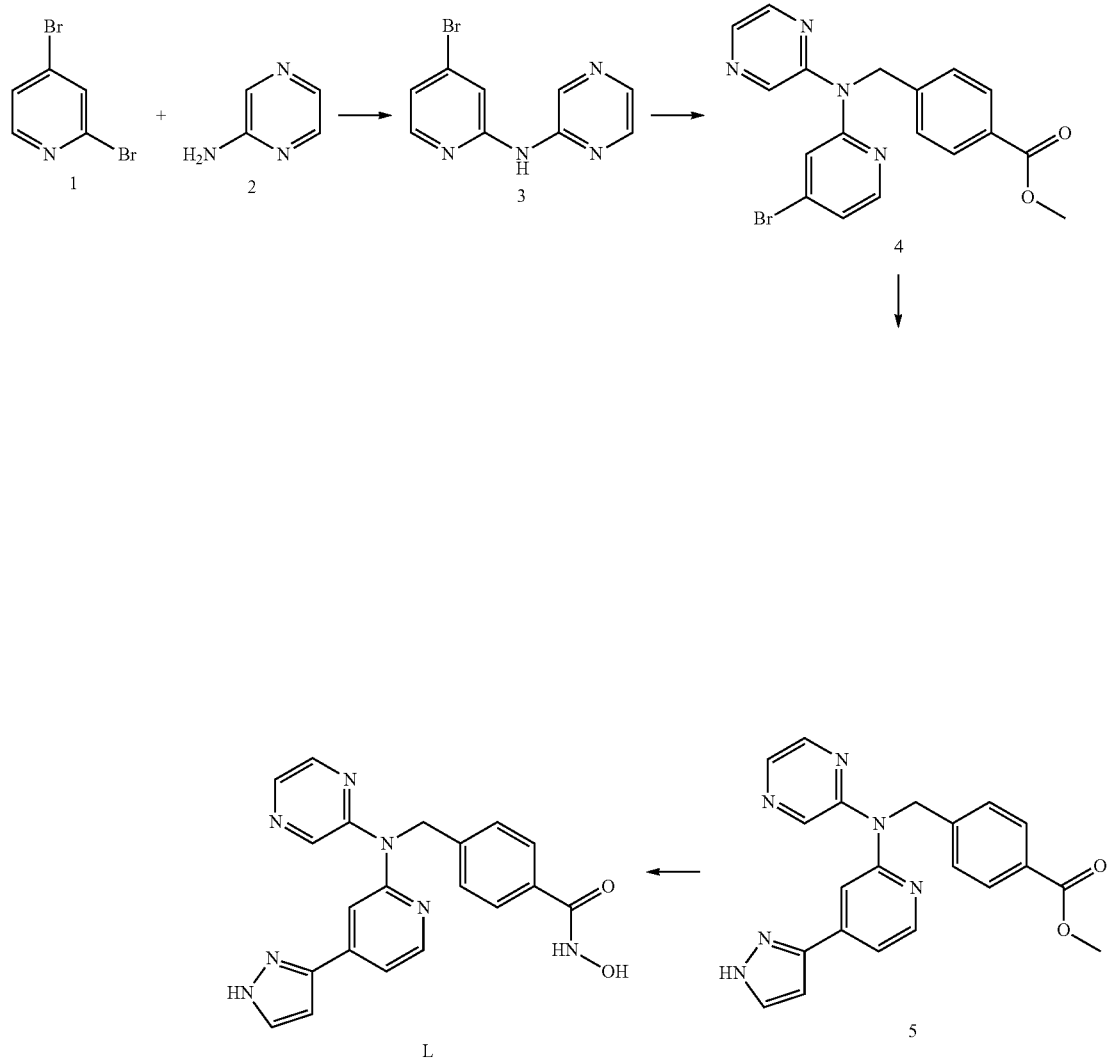

To a suspension of (4) (200 mg, 0.50 mmol), (1H-pyrazol-3-yl)boronic acid hydrochloride (89 mg, 0.6 mmol) and Cs$_2$CO$_3$ (326 mg, 1.0 mmol) in DMF (4 mL) and H$_2$O (1 mL) was added Pd(PPh$_3$)$_4$ (58 mg, 0.05 mmol). The reaction mixture was flushed with N$_2$(g) and heated up to 90° C. for 2 h. Once cooled down, it was partitioned between H$_2$O (15 mL) and IPA/CHCl$_3$ (1:2, 3×30 mL). The combined organic extracts were dried over MgSO$_4$, filtered and concentrated in vacuo. Purification by SCX with MeOH followed by 1N NH$_3$ in MeOH yielded (5) (138 mg, 51%) as a yellow gum.

1H NMR (500 MHz, DMSO-d$_6$), δ$_H$ ppm: 13.14 (br. s., 1H), 8.66-8.68 (m, 1H), 8.33 (d, J=5.3 Hz, 1H), 8.26-8.29 (m, 1H), 8.09-8.13 (m, 1H), 7.87 (d, J=8.3 Hz, 2H), 7.84 (br. s., 1H), 7.69-7.71 (m, 1H), 7.47-7.50 (m, 3H), 6.86 (br. s., 1H), 6.25 (t, J=1.9 Hz, 1H), 5.53 (s, 2H), 3.80 (s, 3H).

LCMS (ES): Found 387.0 [M+H]$^+$.

To a solution of (5) (138 mg, 0.26 mmol) in MeOH/THF (1:1, 1 mL) was added NH$_2$OH (50% in H$_2$O, 0.32 mL, 5.1 mmol) followed by 6N NaOH (0.09 mL, 0.51 mmol). The reaction mixture was stirred at rt for 1 h. It was then quenched with 1M KHSO$_4$ (2 mL) and partitioned between H$_2$O (5 mL) and CH$_2$Cl$_2$ (3×10 mL). The combined organic extracts were dried over MgSO$_4$, filtered and concentrated in vacuo. Purification by reverse prep HPLC yielded Example L (12.7 mg, 24%) as an orange film.

1H NMR (500 MHz, DMSO-d$_6$), δ$_H$ ppm: 13.13 (br. s., 1H), 11.08 (br. s., 1H), 8.95 (br. s., 1H), 8.66 (dd, J=5.1, 1.1 Hz, 1H), 8.32 (d, J=5.2 Hz, 1H), 8.27-8.29 (m, 1H), 8.10 (dd, J=6.6, 2.6 Hz, 1H), 7.80-7.86 (m, 1H), 7.68 (m, 1H), 7.64 (d, J=8.3 Hz, 1H), 7.57 (d, J=8.3 Hz, 1H), 7.45-7.51 (m, 1H), 7.41 (d, J=8.1 Hz, 1H), 7.34 (d, J=8.4 Hz, 1H), 6.85 (d, J=12.1 Hz, 1H), 5.45-5.50 (m, 2H).

LCMS (ES): Found 388.2 [M+H]$^+$.

Example M 4-({[4-(6-Amino-5-fluoropyridin-3-yl)pyridin-2-yl](pyrazin-2-yl)amino}methyl)-N-hydroxybenzamide

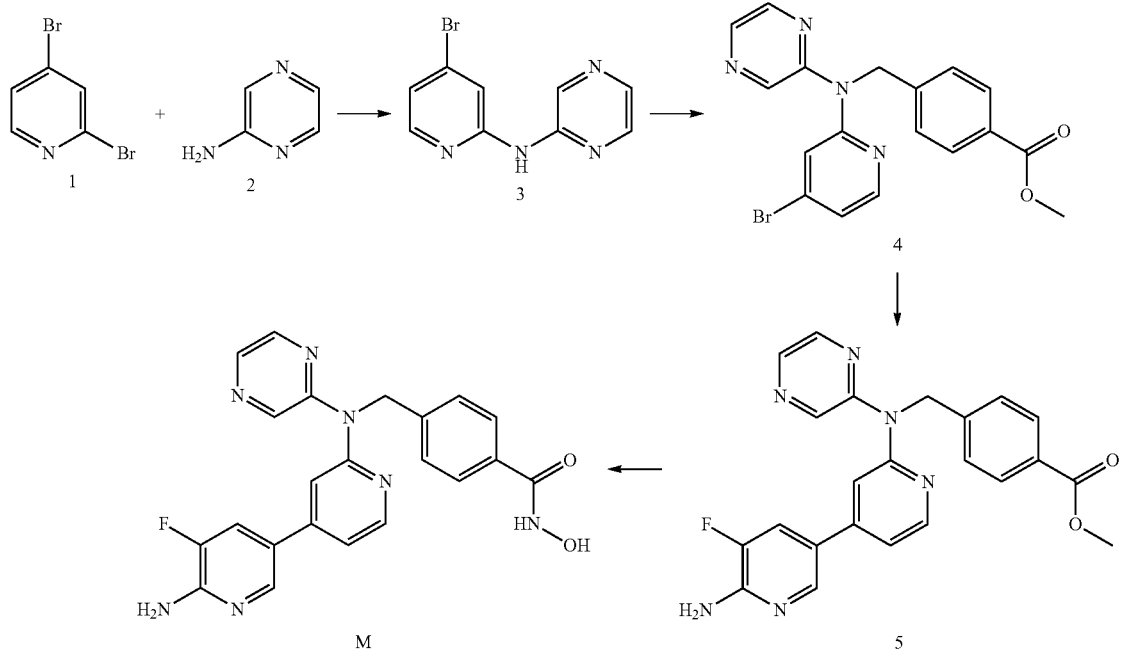

To a suspension of (4) (120 mg, 0.3 mmol), 3-fluoro-5-(tetramethyl-1,3,2-dioxaborolan-2-yl)pyridin-2-amine (86 mg, 0.36 mmol) and $Cs_2CO_3$ (196 mg, 0.6 mmol) in DMF (2 mL) and $H_2O$ (0.5 mL) was added $Pd(PPh_3)_4$ (35 mg, 0.03 mmol). The reaction mixture was flushed with $N_2(g)$ and heated up to 90° C. overnight. Once cooled down, the crude reaction mixture was directly purified by reverse phase column chromatography with $H_2O$/MeCN (19:1-1:1) to yield (5) (68 mg, 53%) as an orange oil.

LCMS (ES): Found 431.1 [M+H]$^+$.

To a solution of (5) (68 mg, 0.16 mmol) in DMSO (3 mL) was added $NH_2OH$ (50% in $H_2O$, 0.43 mL, 14.2 mmol) followed by 6N NaOH (0.02 mL, 0.14 mmol). The reaction mixture was stirred at rt for 1 h. It was then re-treated with $NH_2OH$ (50% in $H_2O$, 0.43 mL, 14.2 mmol) followed by 6N NaOH (0.02 mL, 0.14 mmol) and stirred for an additional 3 h. DMSO (3 mL) was added to the reaction mixture which was directly purified by prep HPLC to yield Example M (11.3 mg, 28%) as a yellow gum.

1H NMR (500 MHz, DMSO-$d_6$), $\delta_H$ ppm: 11.08 (br. s., 1H), 8.96 (br. s., 1H), 8.63 (d, J=1.2 Hz, 1H), 8.29 (d, J=5.3 Hz, 1H), 8.26 (s, 2H), 8.09 (d, J=2.6 Hz, 1H), 7.86 (dd, J=12.7, 1.9 Hz, 1H), 7.61-7.65 (m, 3H), 7.41 (d, J=8.2 Hz, 2H), 7.37 (dd, J=5.3, 1.3 Hz, 1H), 6.63 (s, 2H), 5.51 (s, 2H).

LCMS (ES): Found 432.0 [M+H]$^+$.

Example N 4-({[4-(6-Acetamidopyridin-3-yl)pyridin-2-yl](pyrazin-2-yl)amino}methyl)-N-hydroxybenzamide

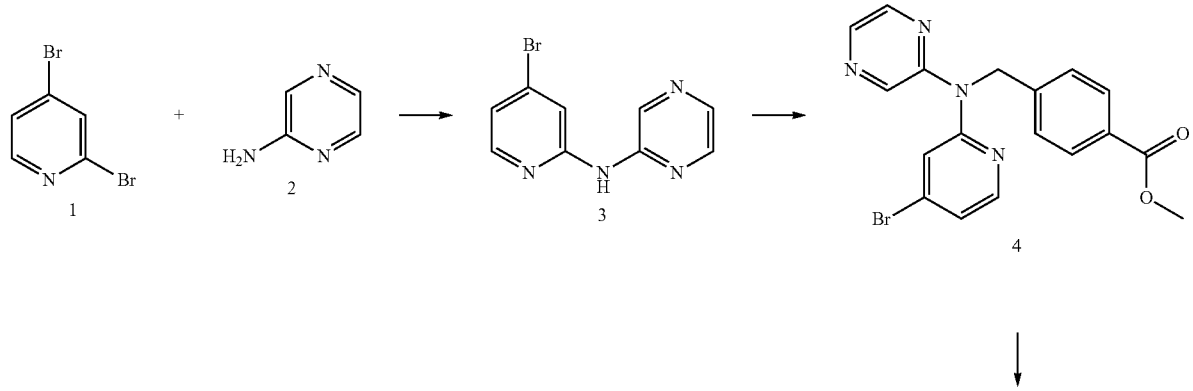

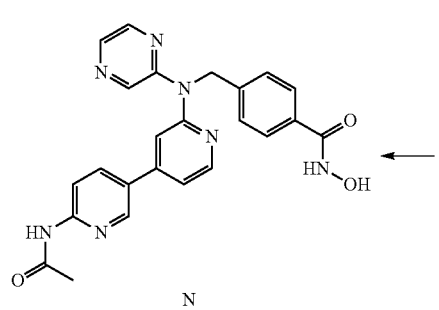
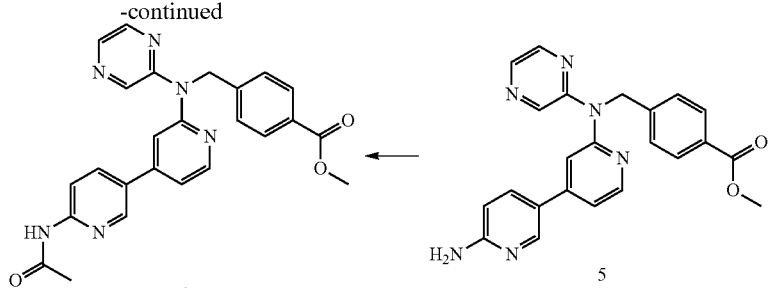

To a suspension of (4) (200 mg, 0.50 mmol), 5-(4,4,5,5-tetramethyl-1,3,2-dioxaborolan-2-yl)pyridin-2-amine (132.3 mg, 0.6 mmol) and Cs$_2$CO$_3$ (326 mg, 1.0 mmol) in DMF (4 mL) and H$_2$O (1 mL) was added Pd(PPh$_3$)$_4$ (58 mg, 0.05 mmol). The mixture was flushed with N$_2$(g) then it was heated up to 90° C. for 2 h. Once cooled down, H$_2$O (20 mL) was added and a precipitate was left to settle at rt for 72 h. After filtration, washings with H$_2$O (2 mL) and drying, (5) (219 mg, quant.) was obtained as a brown solid.

$^1$H NMR (500 MHz, Methanol-d$_4$), $\delta_H$ ppm: 8.54 (s, 1H), 8.31 (d, J=5.3 Hz, 1H), 8.25-8.28 (m, 1H), 8.23 (d, J=2.3 Hz, 1H), 8.02 (d, J=2.6 Hz, 1H), 7.92 (d, J=8.2 Hz, 2H), 7.77 (dd, J=8.8, 2.4 Hz, 1H), 7.50 (s, 1H), 7.48 (d, J=5.5 Hz, 2H), 7.32 (d, J=5.4 Hz, 1H), 6.65 (d, J=8.8 Hz, 1H), 5.55 (s, 2H), 3.86 (s, 3H).

LCMS (ES): Found 413.0 [M+H]$^+$.

To a suspension of (5) (82 mg, 0.20 mmol) in DMF (2 mL) was added triethylamine (0.03 mL, 0.22 mmol). The reaction mixture was stirred at rt for 5 mins, then acetic anhydride (0.02 mL, 0.22 mmol) was added and the reaction mixture was heated up to 50° C. for 42 h. It was then re-treated with triethylamine (0.03 mL, 0.22 mmol), acetic anhydride (0.02 mL, 0.22 mmol) and heated up to 60° C. for 76 h. It was re-treated another time with triethylamine (0.03 mL, 0.22 mmol), acetic anhydride (0.02 mL, 0.22 mmol) and heated up to 90° C. for 24 h. Once cooled down, the crude reaction mixture was partitioned between H$_2$O (15 mL) and CH$_2$Cl$_2$ (3×10 mL). The combined organic extracts were dried over MgSO$_4$, filtered and concentrated in vacuo. Purification by flash column chromatography with CH$_2$Cl$_2$/MeOH (1:0-19:1) yielded (6) (52 mg, 52%) as a pale yellow solid.

1H NMR (500 MHz, DMSO-d$_6$), $\delta_H$ ppm: 10.67 (br. s., 1H), 8.71 (t, J=1.6 Hz, 1H), 8.69 (d, J=1.3 Hz, 1H), 8.37 (d, J=5.2 Hz, 1H), 8.28 (dd, J=2.5, 1.5 Hz, 1H), 8.17 (d, J=1.3 Hz, 2H), 8.12 (d, J=2.6 Hz, 1H), 7.87 (d, J=8.3 Hz, 2H), 7.69 (s, 1H), 7.51 (d, J=8.3 Hz, 2H), 7.44 (dd, J=5.3, 1.3 Hz, 1H), 5.57 (s, 2H), 3.80 (s, 3H), 2.12 (s, 3H).

LCMS (ES): Found 455.1 [M+H]$^+$.

To a solution of (6) (52 mg, 0.11 mmol) in MeOH/THF (1:1, 1.5 mL) was added NH$_2$OH (50% in H$_2$O, 0.14 mL, 2.3 mmol) followed by 6N NaOH (0.04 mL, 0.23 mmol). The reaction mixture was stirred at rt for 1 h. It was then quenched with 1M KHSO$_4$ (2 mL) and partitioned between H$_2$O (5 mL) and CH$_2$Cl$_2$ (2×20 mL). The combined organic extracts were dried over MgSO$_4$, filtered and concentrated in vacuo. Purification by prep HPLC yielded Example N (2.3 mg, 4%) as a yellow oil.

1H NMR (500 MHz, DMSO-d$_6$), C$_H$ ppm: 11.08 (br. s., 1H), 10.67 (br. s., 1H), 8.95 (br. s., 1H), 8.72 (t, J=1.6 Hz, 1H), 8.66-8.68 (m, 1H), 8.37 (d, J=5.2 Hz, 1H), 8.28-8.30 (m, 1H), 8.15-8.18 (m, 2H), 8.10-8.12 (m, 1H), 7.70 (s, 1H), 7.56-7.66 (m, 2H), 7.35-7.44 (m, 3H), 5.49-5.55 (m, 2H), 2.11-2.13 (m, 3H).

LCMS (ES): Found 456.0 [M+H]$^+$.

Example O 4-({[4-(2-Acetamidopyridin-4-yl)pyridin-2-yl](pyrazin-2-yl)amino}methyl)-N-hydroxybenzamide

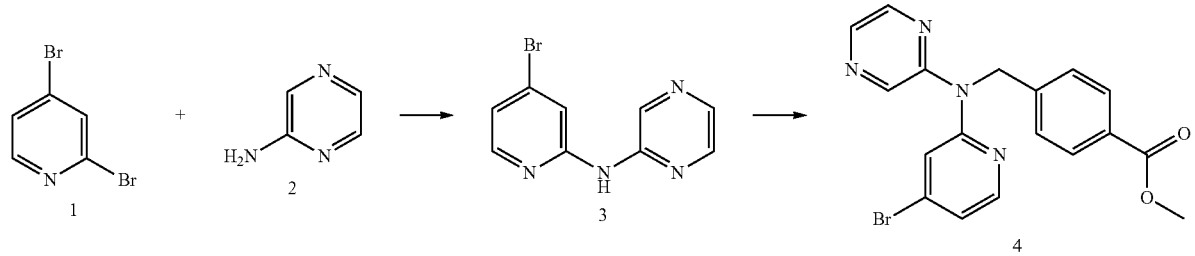

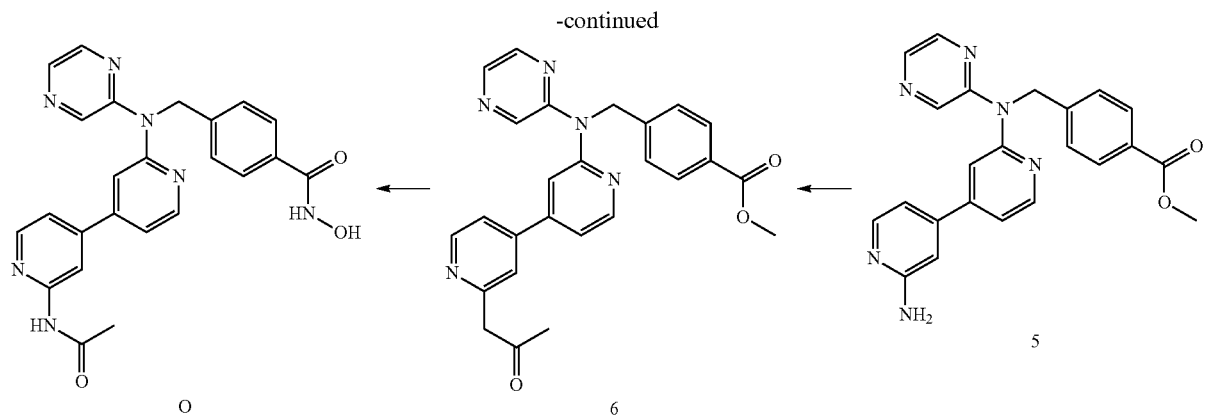

To a suspension of (4) (200 mg, 0.50 mmol), 4-(4,4,5,5-tetramethyl-1,3,2-dioxaborolan-2-yl)pyridin-2-amine (132.3 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The mixture was flushed with $N_2(g)$ then it was heated up to 90° C. for 2 h. Once cooled down, $H_2O$ (20 mL) was added and a precipitate was left to settle at rt for 3 h. After filtration, washings with $H_2O$ (2 mL) and drying, a pale orange solid was obtained, which was purified by flash column chromatography with heptane/EtOAc (4:1-0:1) then EtOAc/MeOH (1:0-7:3) to give (5) (82 mg, 40%) as a yellow solid.

1H NMR (500 MHz, Methanol-$d_4$), $\delta_H$ ppm: 8.60 (s, 1H), 8.41 (d, J=5.2 Hz, 1H), 8.29 (d, J=1.3 Hz, 1H), 8.06 (d, J=2.5 Hz, 1H), 7.97 (d, J=5.4 Hz, 1H), 7.93 (d, J=8.3 Hz, 2H), 7.53 (s, 1H), 7.49 (d, J=8.1 Hz, 2H), 7.34 (d, J=5.2 Hz, 1H), 6.81-6.84 (m, 1H), 6.81 (s, 1H), 5.58 (s, 2H), 3.86 (s, 3H).

LCMS (ES): Found 413.0 $[M+H]^+$.

To a suspension of (5) (100 mg, 0.24 mmol) in $CH_2Cl_2$ (3 mL) and DMF (1 mL) was added triethylamine (0.04 mL, 0.27 mmol). The reaction mixture was stirred at rt for 5 mins, then acetic anhydride (0.02 mL, 0.27 mmol) was added and the reaction mixture was stirred at rt for 18 h then heated up to 50° C. for 5 h, then to 60° C. for an additional 49 h. Once cooled down, the crude reaction mixture was partitioned between $H_2O$ (10 mL) and $CH_2Cl_2$ (3×10 mL). The combined organic extracts were dried over $MgSO_4$, filtered and concentrated in vacuo. Purification by flash column chromatography with heptane/EtOAc (1:0-0:1) then $CH_2Cl_2$/MeOH (1:0-9:1) yielded (6) (56 mg, 50%) as a yellow gum.

1H NMR (500 MHz, DMSO-$d_6$), $\delta_H$ ppm: 10.63 (s, 1H), 8.72 (d, J=1.4 Hz, 1H), 8.42 (dd, J=10.6, 5.2 Hz, 2H), 8.37 (s, 1H), 8.31 (dd, J=2.6, 1.5 Hz, 1H), 8.16 (d, J=2.6 Hz, 1H), 7.88 (d, J=8.3 Hz, 2H), 7.62 (s, 1H), 7.52 (d, J=8.3 Hz, 2H), 7.41 (dd, J=5.2, 1.6 Hz, 1H), 7.34 (dd, J=5.2, 1.4 Hz, 1H), 5.57 (s, 2H), 3.80 (s, 3H), 2.12 (s, 3H).

LCMS (ES): Found 455.1 $[M+H]^+$.

To a solution of (6) (55 mg, 0.12 mmol) in MeOH/THF (1:1, 2 mL) was added $NH_2OH$ (50% in $H_2O$, 0.15 mL, 2.4 mmol) followed by 6N NaOH (0.04 mL, 0.24 mmol). The reaction mixture was stirred at rt for 1.5 h then re-treated twice with $NH_2OH$ (50% in $H_2O$, 0.07 mL, 1.2 mmol) and stirred at rt for an additional 5 h. It was quenched with 1M $KHSO_4$ (2 mL) and partitioned between $H_2O$ (5 mL) and IPA/$CHCl_3$ (1:1, 5×10 mL). The combined organic extracts were dried over $MgSO_4$, filtered and concentrated in vacuo. Purification by prep HPLC yielded Example O (15.9 mg, 29%) as a yellow solid.

1H NMR (500 MHz, DMSO-$d_6$), $\delta_H$ ppm: 11.08 (s, 1H), 10.63 (d, J=8.9 Hz, 1H), 8.95 (s, 1H), 8.71 (d, J=1.3 Hz, 1H), 8.38-8.46 (m, 2H), 8.37 (s, 1H), 8.30 (dd, J=2.6, 1.5 Hz, 1H), 8.14 (dd, J=8.3, 2.6 Hz, 1H), 7.54-7.68 (m, 3H), 7.30-7.46 (m, 4H), 5.52 (m, 2H), 2.12 (s, 3H).

LCMS (ES): Found 456.3 $[M+H]^+$.

Example P 4-({[4-(6-Aminopyridin-3-yl)pyridin-2-yl](pyrazin-2-yl)amino}methyl)-3-fluoro-N-hydroxybenzamide

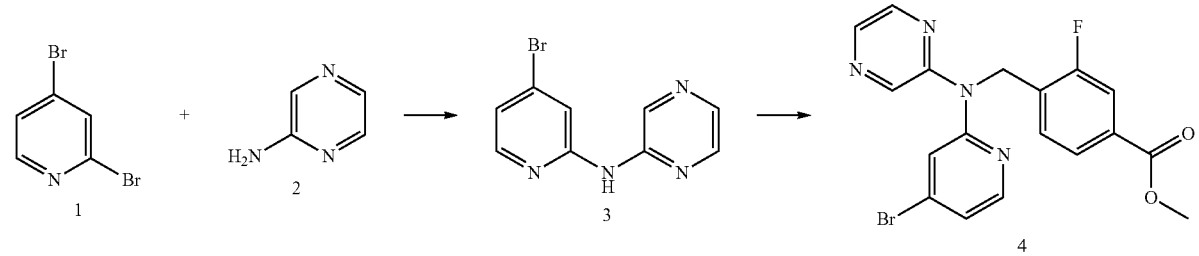

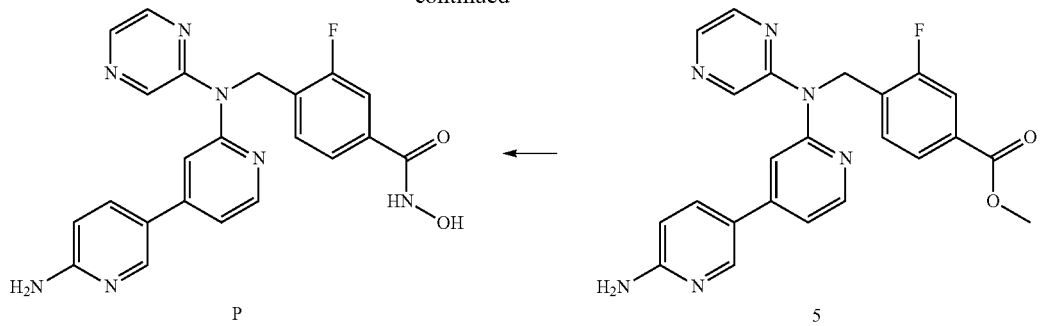

To a solution of (3) (3.96 g, 13.7 mmol) in dry DMF (90 mL) was added NaH (60%, 0.65 g, 12.3 mmol) portion-wise at 5° C. under $N_2$(g). The reaction mixture was stirred for 20 mins, then methyl 4-(bromomethyl)-3-fluorobenzoate (4.4 g, 17.8 mmol) was slowly added. The reaction mixture was stirred for an additional 1 h. It was then partitioned between $H_2O$ (400 mL) and EtOAc (3×250 mL). The combined organic extracts were washed with brine (300 mL), dried over $Na_2SO_4$, filtered and concentrated in vacuo. Purification by flash column chromatography with heptane/EtOAc (1:0-3:1) yielded (4) (4.2 g, 73%) as an off-white solid.

1H NMR (400 MHz, Chloroform-d), $\delta_H$ ppm: 8.69 (d, J=1.4 Hz, 1H), 8.24 (m, 1H), 8.15 (m, 2H), 7.69-7.77 (m, 2H), 7.26-7.36 (m, 2H), 7.12 (dd, J=5.3, 1.5 Hz, 1H), 5.52 (s, 2H), 3.89 (s, 3H).

LCMS (ES): Found 417.0; 419.0 [M+H]$^+$.

To a suspension of (4) (700 mg, 1.7 mmol), 5-(4,4,5,5-tetramethyl-1,3,2-dioxaborolan-2-yl)pyridin-2-amine (720 mg, 3.27 mmol) and $Cs_2CO_3$ (1.1 g, 3.4 mmol) in DMF (14 mL) and $H_2O$ (3.5 mL) was added Pd(PPh$_3$)$_4$ (194 mg, 0.17 mmol). The reaction mixture was flushed with Ar(g) and heated up to 90° C. for 2 h. Once cooled down, it was partitioned between $H_2O$ (50 mL) and EtOAc (3×50 mL). The combined organic extracts were washed with brine (30 mL), dried over $Na_2SO_4$, filtered and concentrated in vacuo. Purification by flash column chromatography with $CH_2Cl_2$/MeOH (1:0-9:1) yielded (5) (430 mg, 59%) as a yellow solid.

1H NMR (400 MHz, Chloroform-d), $\delta_H$ ppm: 8.69 (d, J=1.3 Hz, 1H), 8.34 (d, J=5.2 Hz, 1H), 8.32 (d, J=2.2 Hz, 1H), 8.21 (m, 1H), 8.10 (d, J=2.6 Hz, 1H), 7.62-7.71 (m, 3H), 7.40 (t, J=7.7 Hz, 1H), 7.30 (s, 1H), 7.15 (dd, J=5.2, 1.4 Hz, 1H), 6.57 (d, J=8.6 Hz, 1H), 5.58 (s, 2H), 4.63 (m, 2H), 3.89 (s, 3H).

LCMS (ES): Found 431.1 [M+H]$^+$.

To a solution of (5) (330 mg, 0.77 mmol) in MeOH/THF (1:1, 12 mL) was added $NH_2OH$ (50% in $H_2O$, 1.88 mL, 30.7 mmol) followed by 6N NaOH (0.26 mL, 1.53 mmol). The reaction mixture was stirred at rt for 15 mins. It was quenched with 1M KHSO$_4$ (12 mL) and partitioned between $H_2O$ (35 mL) and $CH_2Cl_2$ (3×25 mL). The combined organic extracts were dried over $Na_2SO_4$, filtered and concentrated in vacuo. The residue was stirred in $Et_2O$ (10 mL) for 3 h, the solids were filtered off, washed with $Et_2O$ (2×5 mL) and dried in vacuo to yield Example P (280 mg, 85%) as an off-white solid.

1H NMR (400 MHz, DMSO-d$_6$), $\delta_H$ ppm: 11.21 (br. s., 1H), 9.11 (br. s., 1H), 8.65 (d, J=1.3 Hz, 1H), 8.39 (d, J=2.5 Hz, 1H), 8.29 (d, J=5.3 Hz, 1H), 8.23-8.27 (m, 13H), 8.09 (d, J=2.8 Hz, 1H), 7.81 (dd, J=8.7, 2.7 Hz, 1H), 7.62 (s, 1H), 7.50 (d, J=11.1 Hz, 1H), 7.32-7.46 (m, 3H), 6.51 (d, J=8.6 Hz, 1H), 6.37 (s, 2H), 5.51 (s, 2H).

LCMS (ES): Found 432.1 [M+H]$^+$.

Example Q 4-({[4-(2-Aminopyridin-4-yl)pyridin-2-yl](pyrazin-2-yl)amino}methyl)-3-fluoro-N-hydroxybenzamide

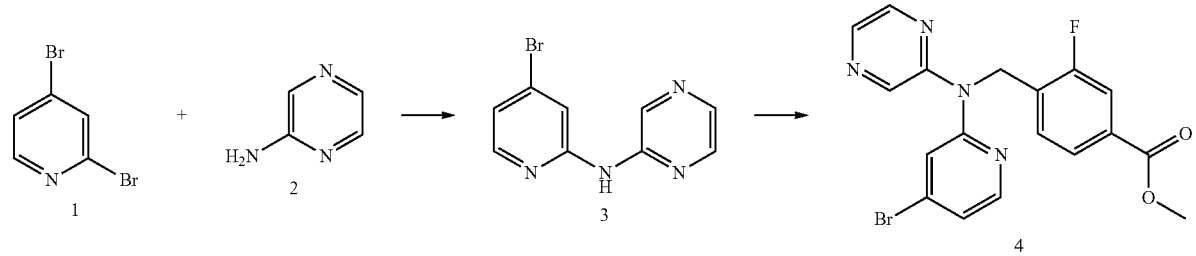

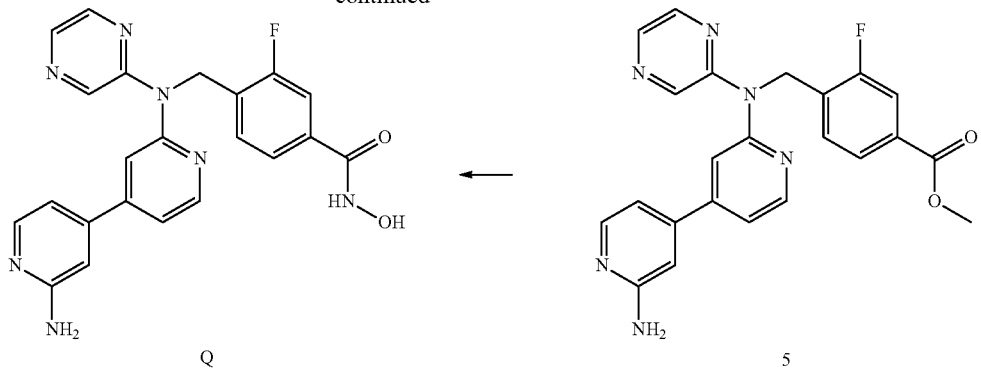

To a suspension of (4) (700 mg, 1.7 mmol), 4-(4,4,5,5-tetramethyl-1,3,2-dioxaborolan-2-yl)pyridin-2-amine (720 mg, 3.27 mmol) and $Cs_2CO_3$ (1.1 g, 3.4 mmol) in DMF (14 mL) and $H_2O$ (3.5 mL) was added $Pd(PPh_3)_4$ (194 mg, 0.17 mmol). The reaction mixture was flushed with Ar(g) and heated up to 90° C. for 2 h. Once cooled down, it was partitioned between $H_2O$ (50 mL) and EtOAc (3×50 mL). The combined organic extracts were washed with brine (30 mL), dried over $Na_2SO_4$, filtered and concentrated in vacuo. Purification by flash column chromatography with $CH_2Cl_2$/MeOH (1:0-19:1) yielded (5) (340 mg, 46%) as a yellow oil.

1H NMR (400 MHz, Chloroform-d), $\delta_H$ ppm: 8.70 (m, 1H), 8.42 (d, J=5.2 Hz, 1H), 8.23 (m, 1H), 8.15 (d, J=5.3 Hz, 1H), 8.11 (d, J=2.5 Hz, 1H), 7.69-7.71 (m, 2H), 7.40 (t, J=7.6 Hz, 1H), 7.35 (m, 1H), 7.16 (d, J=5.1 Hz, 1H), 6.79 (d, J=5.2 Hz, 1H), 6.62 (s, 1H), 5.59 (s, 2H), 5.30 (m, 1H), 4.57 (m, 1H), 3.89 (s, 3H).

LCMS (ES): Found 431.1 [M+H]+.

To a solution of (5) (300 mg, 0.70 mmol) in MeOH/THF (1:1, 12 mL) was added $NH_2OH$ (50% in $H_2O$, 1.71 mL, 27.9 mmol) followed by 6N NaOH (0.23 mL, 1.39 mmol). The reaction mixture was stirred at rt for 15 mins. It was quenched with 1M $KHSO_4$ (12 mL) and partitioned between $H_2O$ (35 mL) and $CH_2Cl_2$ (3×25 mL). The combined organic extracts were dried over $Na_2SO_4$, filtered and concentrated in vacuo. The residue was stirred in $Et_2O$ (10 mL) for 3 h, the solids were filtered off, washed with $Et_2O$ (2×5 mL) and dried in vacuo to yield Example Q (191 mg, 59%) as an off-white solid.

1H NMR (400 MHz, DMSO-d$_6$), $\delta_H$ ppm: 11.23 (br. s., 1H), 9.11 (br. s., 1H), 8.71 (d, J=1.5 Hz, 1H), 8.41 (d, J=5.3 Hz, 1H), 8.30 (dd, J=2.5, 1.5 Hz, 1H), 8.15 (d, J=2.5 Hz, 1H), 8.01 (d, J=5.3 Hz, 1H), 7.61 (s, 1H), 7.49-7.54 (m, 1H), 7.43-7.47 (m, 1H), 7.35-7.42 (m, 1H), 7.32 (dd, J=5.2, 1.1 Hz, 1H), 6.81 (dd, J=5.4, 1.6 Hz, 1H), 6.71 (s, 1H), 6.10 (s, 2H), 5.53 (s, 2H).

LCMS (ES): Found 432.2 [M+H]+.

Example R 4-({[4-(6-Acetamidopyridin-3-yl)pyridin-2-yl](pyrazin-2-yl)amino}methyl)-3-fluoro-N-hydroxybenzamide

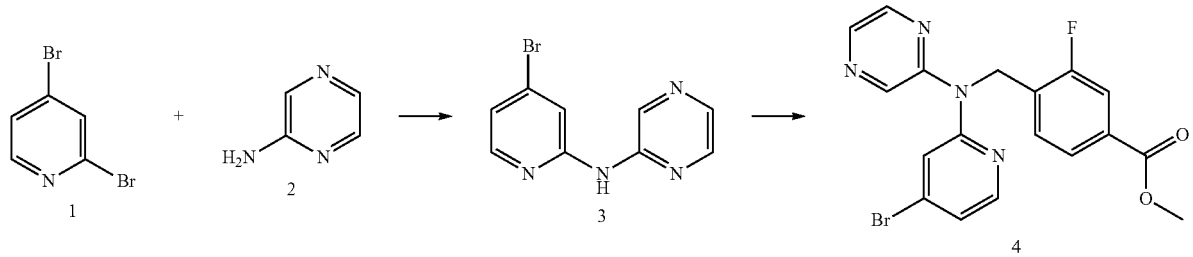

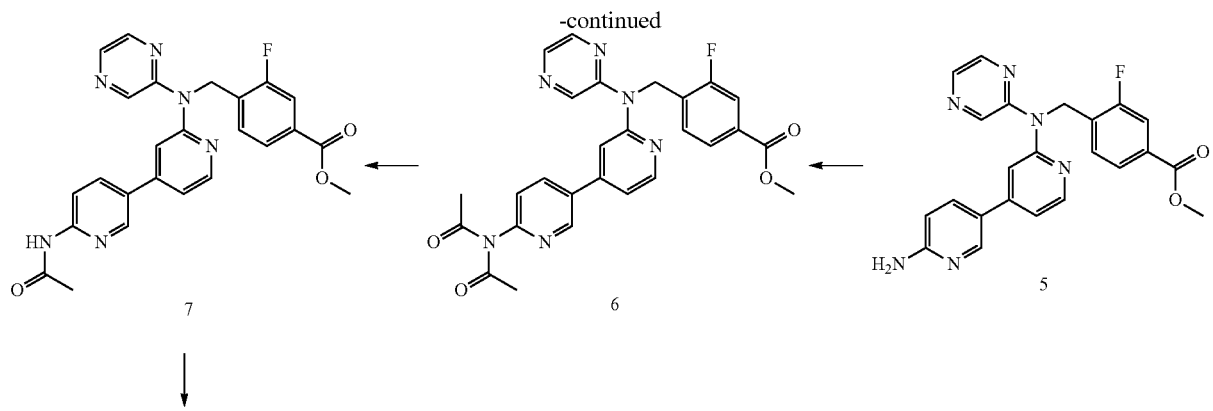

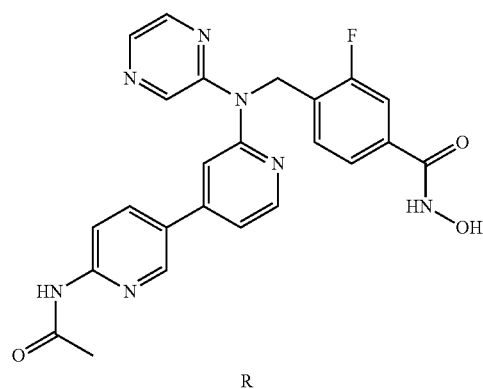

To a solution of (5) (52 mg, 0.12 mmol) in CH$_2$Cl$_2$ (2 mL) was added acetyl chloride (0.009 mL, 0.13 mmol) and triethylamine (0.002 mL, 0.14 mmol) at rt. The reaction mixture was heated up to 40° C. for 3 h. It was then re-treated twice with acetyl chloride (0.009 mL, 0.13 mmol) and triethylamine (0.002 mL, 0.14 mmol) and heated back up to 40° C. for an additional 48 h and 3 h. The solvents were removed in vacuo and the crude reaction mixture was partitioned between H$_2$O (5 mL) and EtOAc (3×10 mL). The combined organic extracts were washed with brine (30 mL), dried over Na$_2$SO$_4$, filtered and concentrated in vacuo to yield (6) (62 mg, quant.) as a brown oil.

LCMS (ES): Found 515.2 [M+H]$^+$.

To a solution of (6) (62 mg, 0.12 mmol) in THF (2 mL) was added NH$_4$OH (32% in H$_2$O, 0.14 mL, 1.15 mmol) at rt. The reaction mixture was stirred at rt for 1 h to completion. It was acidified to pH-1 by addition of 1N HCl, then basified to pH-8 by addition of saturated NaHCO$_3$. It was then partitioned between H$_2$O (10 mL) and EtOAc (3×15 mL). The combined organic extracts were dried over Na$_2$SO$_4$, filtered and concentrated in vacuo to yield (7) (40 mg, 71%) as a white foam.

LCMS (ES): Found 473.2 [M+H]$^+$.

To a solution of (7) (40 mg, 0.10 mmol) in MeOH/THF (1:1, 3 mL) was added NH$_2$OH (50% in H$_2$O, 0.29 mL, 4.8 mmol) followed by 6N NaOH (0.04 mL, 0.24 mmol). The reaction mixture was stirred at rt for 20 mins. It was quenched with 1M KHSO$_4$ (12 mL) and partitioned between H$_2$O (35 mL) and CH$_2$Cl$_2$ (3×25 mL). The combined organic extracts were dried over Na$_2$SO$_4$, filtered and concentrated in vacuo. Purification by prep HPLC yielded Example R (22 mg, 55%) as a white solid.

1H NMR (400 MHz, DMSO-d$_6$), $\delta_H$ ppm: 11.23 (br. s., 1H), 10.72 (s, 1H), 8.93-9.31 (m, 1H), 8.76 (s, 1H), 8.70 (d, J=1.0 Hz, 1H), 8.39 (d, J=5.3 Hz, 1H), 8.28 (dd, J=2.5, 1.5 Hz, 1H), 8.15-8.24 (m, 2H), 8.12 (d, J=2.5 Hz, 1H), 7.78 (s, 1H), 7.32-7.56 (m, 4H), 5.54 (s, 2H), 2.12 (s, 3H).

LCMS (ES): Found 474.2 [M+H]$^+$.

Example S 4-({[4-(2-Acetamidopyridin-4-yl)pyridin-2-yl](pyrazin-2-yl)amino}methyl)-3-fluoro-N-hydroxybenzamide

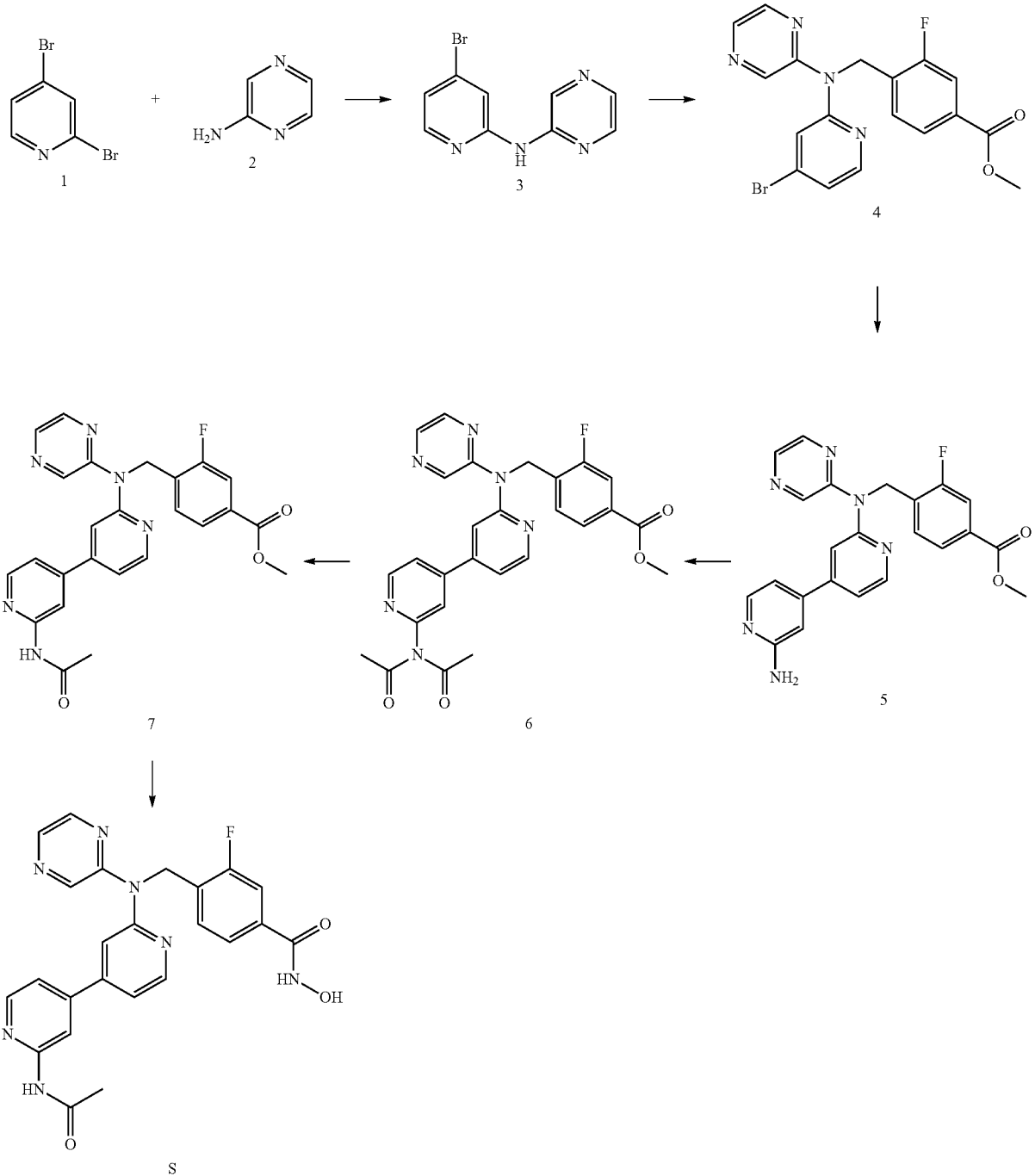

To a solution of (5) (205 mg, 0.43 mmol) in CH₂Cl₂ (4 mL) was added acetyl chloride (0.04 mL, 0.51 mmol) and triethylamine (0.07 mL, 0.51 mmol) at rt. The reaction mixture was stirred at rt for 18 h. It was then re-treated with acetyl chloride (0.04 mL, 0.51 mmol) and triethylamine (0.07 mL, 0.51 mmol) and heated up to 40° C. for 5 h. The solvents were removed in vacuo and the residue was partitioned between H₂O (5 mL) and EtOAc (3×10 mL). The combined organic extracts were washed with brine (30 mL), dried over Na₂SO₄, filtered and concentrated in vacuo. Purification by flash column chromatography with heptane/EtOAc (19:1-0:1) yielded (6) (100 mg, 45%) as a colourless oil.

LCMS (ES): Found 515.2 [M+H]⁺.

To a solution of (6) (100 mg, 0.19 mmol) in THF (2 mL) was added NH₄OH (32% in H₂O, 0.06 mL, 0.49 mmol) at rt. The reaction mixture was stirred at rt for 30 mins to completion. It was acidified to pH-1 by addition of 1N HCl, then basified to pH-8 by addition of saturated NaHCO₃. It was then partitioned between H₂O (10 mL) and EtOAc (3×15 mL). The combined organic extracts were dried over Na₂SO₄, filtered and concentrated in vacuo to yield (7) (88 mg, 96%) as a white foam.

LCMS (ES): Found 473.2 [M+H]⁺.

To a solution of (7) (88 mg, 0.19 mmol) in MeOH/THF (1:1, 4 mL) was added NH₂OH (50% in H₂O, 0.46 mL, 7.5 mmol) followed by 6N NaOH (0.06 mL, 0.37 mmol). The reaction mixture was stirred at rt for 15 mins. It was quenched with 1M KHSO₄ (12 mL) and partitioned between H₂O (35 mL) and CH₂Cl₂ (3×25 mL). The combined organic extracts were dried over Na₂SO₄, filtered and concentrated in vacuo. Purification by prep HPLC yielded Example S (39 mg, 44%) as a white solid.

1H NMR (400 MHz, DMSO-d₆), δ_H ppm: 11.24 (br. s., 1H), 10.67 (s, 1H), 9.13 (br. s., 1H), 8.73 (d, J=1.0 Hz, 1H), 8.45 (d, J=5.3 Hz, 1H), 8.42 (d, J=5.3 Hz, 1H), 8.38 (s, 1H), 8.29-8.32 (m, 1H), 8.16 (d, J=2.5 Hz, 1H), 7.69 (s, 1H), 7.51 (m, 1H), 7.43-7.47 (m, 2H), 7.41 (d, J=7.8 Hz, 1H), 7.35-7.39 (m, 1H), 5.55 (s, 2H), 2.12 (s, 3H).

LCMS (ES): Found 474.2 [M+H]⁺.

Example T

3-Fluoro-N-hydroxy-4-({[4-(6-methanesulfonami-dopyridin-3-yl)pyridin-2-yl](pyrazin-2-yl)amino}methyl)benzamide

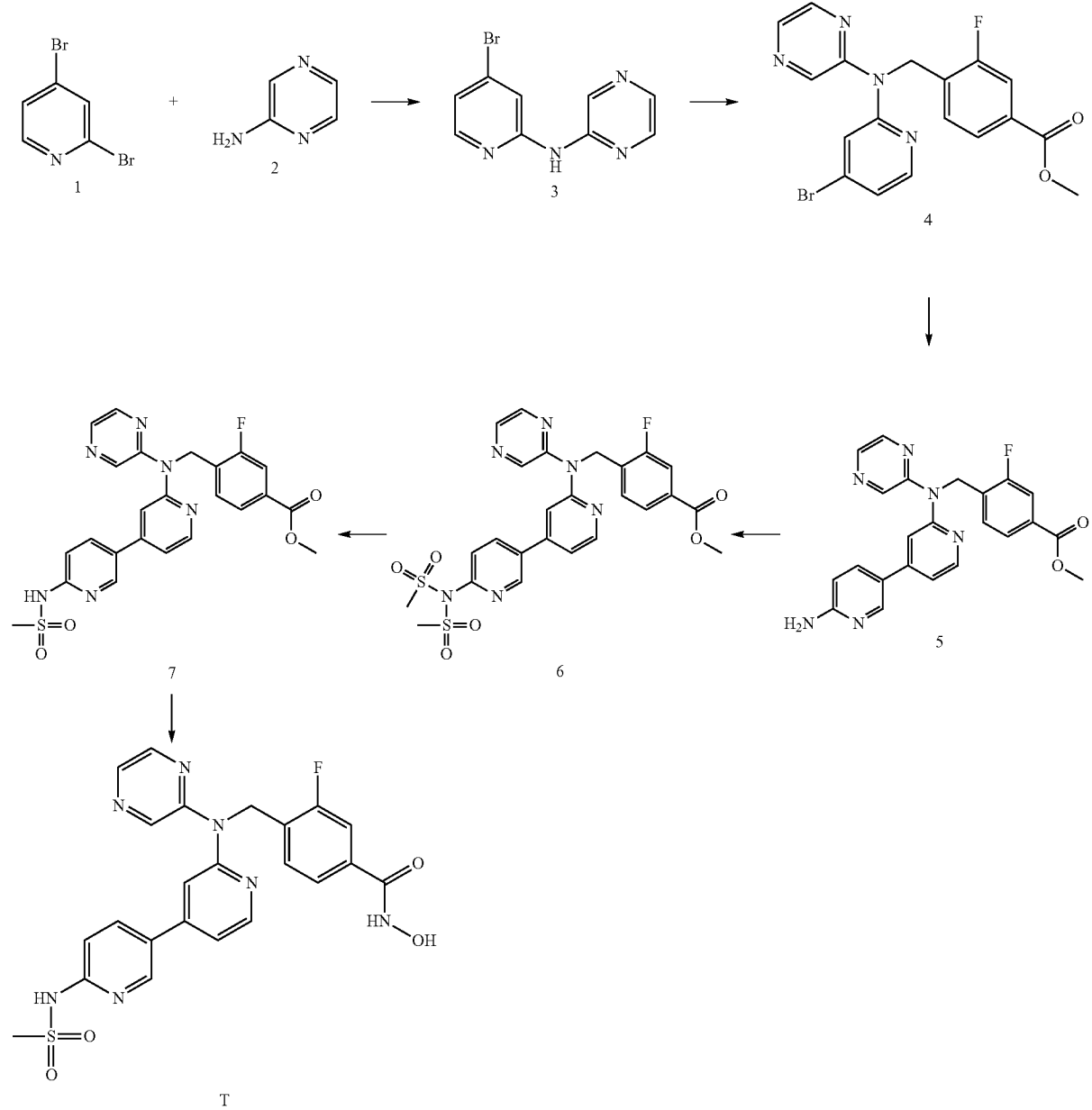

To a solution of (5) (201 mg, 0.47 mmol) and triethylamine (0.19 mL, 1.4 mmol) in EtOAc (2 mL) was added mesyl chloride (0.07 mL, 0.93 mmol) at 0° C. The reaction mixture was stirred for 1 h. It was then re-treated with mesyl chloride (0.07 mL, 0.93 mmol), triethylamine (0.19 mL, 1.4 mmol) and stirred for another 1 h. The reaction mixture was partitioned between H$_2$O (5 mL) and EtOAc (3×10 mL). The combined organic extracts were dried over Na$_2$SO$_4$, filtered and concentrated in vacuo to yield (6) (239 mg, 79%) as a brown foam.

LCMS (ES): Found 587.1 [M+H]$^+$.

To a solution of (6) (237 mg, 0.40 mmol) in MeOH (3.4 mL) was added 1N NaOH (2.02 mL, 2.02 mmol). The reaction mixture was stirred at rt for 10 mins to completion. It was acidified to pH-4 by addition of 2N HCl, then basified to pH-8 by addition of saturated NaHCO$_3$. It was then partitioned between H$_2$O (10 mL) and CH$_2$Cl$_2$ (3×15 mL). The combined organic extracts were dried over Na$_2$SO$_4$, filtered and concentrated in vacuo. Purification by flash column chromatography with EtOAc yielded (7) (178 mg, 81%) as a beige solid.

LCMS (ES): Found 509.2 [M+H]$^+$.

To a solution of (7) (178 mg, 0.35 mmol) in MeOH/THF (1:1, 12 mL) was added NH$_2$OH (50% in H$_2$O, 0.86 mL, 14.0 mmol) followed by 6N NaOH (0.12 mL, 0.70 mmol). The reaction mixture was stirred at rt for 1 h. Then, it was re-treated with NH$_2$OH (50% in H$_2$O, 0.21 mL, 7.0 mmol) followed by 6N NaOH (0.06 mL, 0.35 mmol) and stirred for another 20 mins. It was quenched with 1M KHSO$_4$ (16 mL) and partitioned between H$_2$O (35 mL) and CH$_2$Cl$_2$/MeOH (9:1, 3×25 mL). The combined organic extracts were dried over Na$_2$SO$_4$, filtered and concentrated in vacuo. Purification by prep HPLC yielded Example T (36 mg, 20%).

1H NMR (400 MHz, DMSO-d$_6$), δ$_H$ ppm: 10.85 (br. s., 1H), 9.02 (br. s, 1H), 8.68 (s, 1H), 8.56 (d, J=1.3 Hz, 1H), 8.32 (d, J=5.3 Hz, 1H), 8.26 (s, 1H), 8.10 (d, J=2.5 Hz, 1H), 7.92 (d, J=8.3 Hz, 1H), 7.66 (s, 1H), 7.50 (m, 1H), 7.42-7.47 (m, 1H), 7.34-7.42 (m, 2H), 6.76 (d, J=8.1 Hz, 1H), 5.52 (s, 2H), 3.07 (s, 3H).

LCMS (ES): Found 510.1 [M+H]$^+$.

Example U

3-Fluoro-N-hydroxy-4-({[4-(2-methanesulfonamidopyridin-4-yl)pyridin-2-yl](pyrazin-2-yl)amino}methyl)benzamide

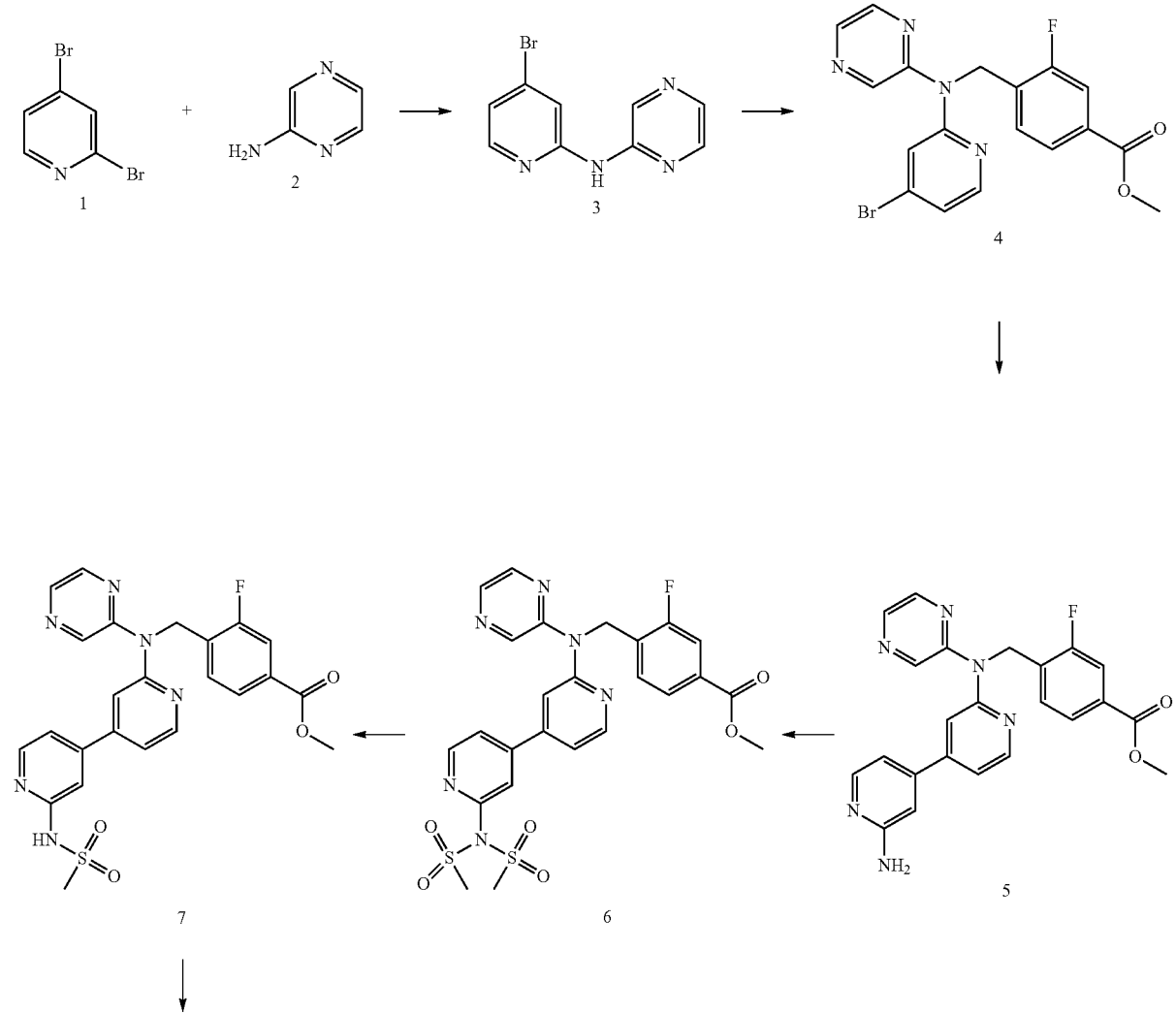

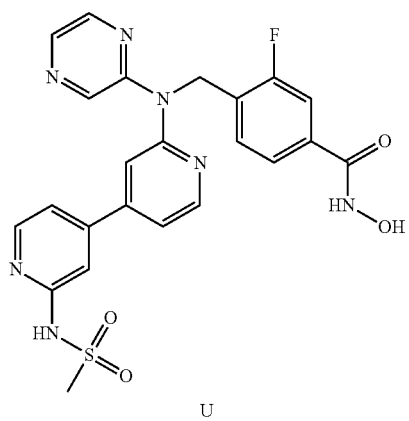

U

To a solution of (5) (250 mg, 0.47 mmol) and triethylamine (0.24 mL, 1.7 mmol) in $CH_2Cl_2$ (10 mL) was added mesyl chloride (0.09 mL, 1.16 mmol) at 0° C. The reaction mixture was stirred for 1 h. It was then re-treated with mesyl chloride (0.09 mL, 1.16 mmol), triethylamine (0.24 mL, 1.7 mmol) and stirred for another 15 min. The reaction mixture was partitioned between $H_2O$ (5 mL) and $CH_2Cl_2$ (3×10 mL). The combined organic extracts were dried over $Na_2SO_4$, filtered and concentrated in vacuo to yield (6) (214 mg, 78%) as a brown oil.

LCMS (ES): Found 587.1 $[M+H]^+$.

To a solution of (6) (214 mg, 0.37 mmol) in MeOH (3.4 mL) was added 1N NaOH (1.82 mL, 1.82 mmol). The reaction mixture was stirred at rt for 20 mins to completion. It was acidified to pH-4 by addition of 2N HCl, then basified to pH-8 by addition of saturated $NaHCO_3$. It was then partitioned between $H_2O$ (10 mL) and $CH_2Cl_2$ (3×15 mL). The combined organic extracts were dried over $Na_2SO_4$, filtered and concentrated in vacuo. Purification by flash column chromatography with EtOAc yielded (7) (200 mg, ~quant.) as a beige foam.

LCMS (ES): Found 509.1 $[M+H]^+$.

To a solution of (7) (200 mg, 0.39 mmol) in MeOH/THF (1:1, 10 mL) was added $NH_2OH$ (50% in $H_2O$, 1.43 mL, 23.6 mmol) followed by 6N NaOH (0.2 mL, 1.18 mmol). The reaction mixture was stirred at rt for 15 mins. Then, it was re-treated with $NH_2OH$ (50% in $H_2O$, 1.43 mL, 23.6 mmol) and stirred for another 40 mins. It was quenched with 1M $KHSO_4$ (16 mL) and partitioned between $H_2O$ (35 mL) and $CH_2Cl_2$/MeOH (9:1, 3×25 mL). The combined organic extracts were dried over $Na_2SO_4$, filtered and concentrated in vacuo. Purification by prep HPLC yielded Example U (34 mg, 17%) as a white solid.

1H NMR (400 MHz, DMSO-$d_6$), $\delta_H$ ppm: 10.63-11.35 (m, 1H), 9.16 (br. s., 1H), 8.73 (d, J=1.3 Hz, 1H), 8.41 (d, J=5.1 Hz, 1H), 8.30 (dd, J=2.4, 1.6 Hz, 1H), 8.17 (d, J=5.1 Hz, 1H), 8.15 (d, J=2.8 Hz, 1H), 7.62 (s, 1H), 7.51 (d, J=11.1 Hz, 1H), 7.45 (d, J=8.1 Hz, 1H), 7.32-7.41 (m, 2H), 6.89-7.05 (m, 2H), 5.54 (s, 2H), 3.04 (s, 3H).

LCMS (ES): Found 510.1 $[M+H]^+$.

Biochemical Assay and Data
1) Assay
i. Biochemical Assay Description

Activity against all zinc-dependent HDACs 1 to 11 was assessed by using an acetylated AMC-labeled peptide substrate. The substrate RHKKAc was used for all class I and IIb HDACs; for HDAC8, the substrate used was RHKAcKAc. Activity against the class IIa HDACs (HDAC4, 5, 7, 9) was determined using a class IIa-specific substrate, Acetyl-Lys(trifluoroacetyl)-AMC (Lahm et al, 2007, PNAS, 104, 17335-17340). All assays were based on the AMC-labeled substrate and developer combination.

The protocol involved a two-step reaction: first, the substrate with the acetylated lysine side chain is incubated with a sample containing HDAC activity, to produce the deacetylated products, which are then digested in the second step by the addition of developer to produce the fluorescent signal proportional to the amount of deacetylated substrates.

ii. Enzymes

Human HDAC1 (GenBank Accession No. NM_004964), full length with C-terminal His-tag and C-terminal FLAG-tag, MW=56 kDa, expressed in baculovirus expression system.

Human HDAC2 (GenBank Accession No. NM_001527), full length with C-terminal His-tag, MW=56 kDa, expressed inbaculovirus expression system.

Complex of human HDAC3 (GenBank Accession No. NM_003883), full length with C-terminal His tag, MW=49.7 kDa, and human NCOR2 (amino acid 395-489) (GenBank Accession No. NM_006312), N-terminal GST tag, MW=37.6 kDa, co-expressed in baculovirus expression system.

Human HDAC4 (GenBank Accession No. NM_006037), amino acids 627-1085 with N-terminal GST tag, MW=75.2 kDa, expressed in baculovirus expression system.

Human HDAC5 (GenBank Accession No. NM_005474), full length with N-terminal GST tag, MW=150 kDa, expressed in baculovirus expression system.

Recombinant human HDAC6 (GenBank Accession No. BC069243), full length, MW=180 kDa, was expressed by baculovirus in Sf9 insect cells using an N-terminal GST tag.

Human HDAC7 (GenBank Accession No. AY302468), (a.a. 518-end) with N-terminal GST tag, MW=78 kDa, expressed in baculovirus expression system.

Human HDAC8 (GenBankAccession No. NM_018486), full length with C-terminal His-tag, MW=46.4 kDa, expressed in a baculovirus expression system.

Human HDAC9 (GenBank Accession No. NM_178423), amino acids 604-1066 with C-terminal His tag, MW=50.7 kDa, expressed in baculovirus expression system.

Human HDAC10 (a.a. 1-481), GenBank Accession No. NM_032019 with N-terminal GST tag and C-terminal His tag, MW=78 kDa, expressed in baculovirus expression system.

Human HDAC11 (full length) (GenBank Accession No. NM_024827) with N-terminal GST tag, MW=66 kDa, expressed in baculovirus expression system.

iii. Reaction Conditions

Assay Buffer: 50 mM Tris-HCl, pH8.0, 137 mM NaCl, 2.7 mM KCl, 1 mM $MgCl_2$. Before use, 1 mg/mL BSA and DMSO are added.

HDAC1: 2.68 nM HDAC1 and 50 m M HDAC substrate are in the reaction buffer with 1% DMSO final. Incubate for 2 hours at 30° C.

HDAC2: 3.33 nM HDAC2 and 50 mM HDAC substrate are in the reaction buffer with 1% DMSO final. Incubate for 2 hours at 30° C.

HDAC3: 1.13 nM HDAC3 and 50 mM HDAC substrate are in the reaction buffer with 1% DMSO final. Incubate for 2 hours at 30° C.

HDAC6: 0.56 nM HDAC6 and 50 mM HDAC substrate are in the reaction buffer with 1% DMSO final. Incubate for 2 hours at 30° C.

HDAC8: 46.4 nM HDAC8 and 50 mM HDAC8 substrate are in the reaction buffer with 1% DMSO final. Incubate for 2 hours at 30° C.

HDAC10: 96.15 nM HDAC10 and 50 mM HDAC substrate are in the reaction buffer with 1% DMSO final. Incubate for 2 hours at 30° C.

HDAC11: 227.27 nM HDAC11 and 50 mMHDAC substrate are in the reaction buffer with 1% DMSO final. Incubate for 2 hours at 30° C.

For class IIa HDACs, assay buffer is the same.

Other reaction conditions are as follows:

HDAC4: 0.03 nM HDAC4 and 50 mM Class IIa HDAC substrate are in the reaction buffer with 1% DMSO final. Incubate for 30 minutes at room temperature.

HDAC5: 0.67 nM HDAC5 and 50 mM Class IIa HDAC substrate are in the reaction buffer with 1% DMSO final. Incubate for 30 minutes at room temperature.

HDAC7: 0.26 nM HDAC7 and 50 mM Class IIa HDAC substrate are in the reaction buffer with 1% DMSO final. Incubate for 30 minutes at room temperature.

HDAC9: 2.37 nM HDAC9 and 50 mM Class IIa HDAC substrate are in the reaction buffer with 1% DMSO final. Incubate for 30 minutes at room temperature.

Control Inhibitor: Trichostatin A (TSA)

Fluorescent Deacetylated Standard: Biomol, Cat#KI-142;

For Standard Control, compound is added at assay concentration to 2.5 uM

Fluorescent Deacetylated Standard; 10 doses in 6 uL

For Fluorescence Background Control, compound is added at assay concentrations to 50 mM HDAC substrate; 10 doses in 6 uL.

Fluorescence background signal is then subtracted from compound data signal.

% Conversion must be between 5% and 15% to obtain optimum result.

iv. Assay Procedure

Stage 1: Deacetylation of substrate by incubation of HDAC enzymes with corn pounds Stage 2: Development by addition of Developer to digest the deacetylated substrate, and generate the fluorescent colour; Detection: 360/460 Ex/Em 2) Inhibition of HDAC Enzymes

| | $IC_{50}$ (nM) HDAC | |
|---|---|---|
| Example | 1 | 6 |
| A | *** | * |
| B | *** | * |
| C | ** | * |
| D | *** | * |
| E | ** | * |
| F | *** | * |
| G | *** | * |
| H | **** | * |
| I | **** | * |
| J | *** | * |
| K | *** | * |
| L | *** | * |
| M | *** | * |
| N | *** | * |
| O | *** | * |
| P | ** | * |
| Q | *** | * |
| R | *** | * |
| S | *** | * |
| T | **** | * |
| U | **** | * |

Key:
**** ≥10 uM
*** ≤10 uM ≥ 1 uM
** ≤1 uM ≥ 500 nM
* ≤500 nM

The invention claimed is:
1. A compound represented by:

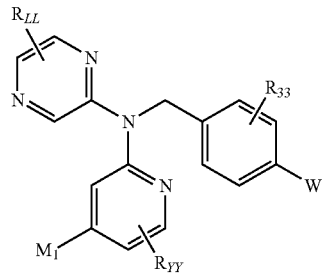

or a pharmaceutically acceptable salt thereof, wherein $M_1$ is a 5-membered monocyclic heteroaryl or a 8-10 membered bicyclic heteroaryl, optionally substituted by one, two or three substituents each independently selected from $R^M$;

$R^M$ is selected for each occurrence from the group consisting of $C_{1-6}$alkyl, $C_{2-6}$alkenyl, $C_{2-6}$alkynyl; $C_{1-6}$alkoxy, $C_{3-6}$cycloalkyl, halogen, $NR^aR^b$; —$NR^a$—C(O)—$R^a$; and —$NR^aSO_2$—$R^a$ (wherein $C_{1-6}$alkyl, $C_{2-6}$alkenyl, $C_{2-6}$alkynyl, $C_{1-6}$alkoxy and $C_{3-6}$cycloalkyl may be optionally substituted by one, two or three halogens);

$R_{33}$ is selected for each occurrence from the group consisting of H, halogen and $C_{1-6}$alkyl (optionally substituted by one, two or three halogens);

W is a zinc binding group;

$R_{LL}$ is selected from the group consisting of H, $CH_3$, and halogen;

$R_{YY}$ is selected from the group consisting of H, $CH_3$, and halogen; and $R^a$ and $R^b$ are each independently selected from H or $C_{1-4}$alkyl; or $R^a$ and $R^b$ taken together with the nitrogen to which they are attached form a 4-6 membered heterocycle.

2. The compound of claim 1, wherein $R^M$ is selected for each occurrence from the group consisting of F, —CH₃, NH₂, —NH—C(O)—CH₃, and —NH—SO₂—CH₃.

3. The compound of claim 1, wherein W is —CONHOH.

4. The compound of claim 1, wherein the compound is represented by:

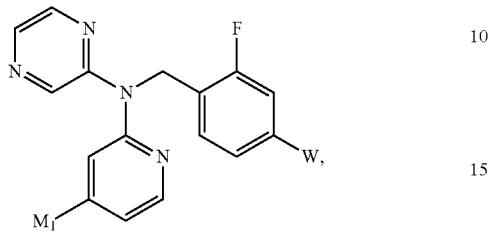

or a pharmaceutically acceptable salt thereof, wherein
M₁ is a 5-membered monocyclic heteroaryl or a 8-10 membered bicyclic heteroaryl, optionally substituted by one, two or three substituents each independently selected from $R^M$;
$R^M$ is selected for each occurrence from the group consisting of $C_{1-6}$alkyl, $C_{2-6}$alkenyl, $C_{2-6}$alkynyl; $C_{1-6}$alkoxy, $C_{3-6}$cycloalkyl, halogen, $NR^aR^b$; —$NR^a$—C(O)—$R^a$; and —$NR^aSO_2$—$R^a$ (wherein $C_{1-6}$alkyl, $C_{2-6}$alkenyl, $C_{2-6}$alkynyl, $C_{1-6}$alkoxy and $C_{3-6}$cycloalkyl may be optionally substituted by one, two or three halogens);
W is a zinc binding group; and
$R^a$ and $R^b$ are each independently selected from H or $C_{1-4}$alkyl; or $R^a$ and $R^b$ taken together with the nitrogen to which they are attached form a 4-6 membered heterocycle.

5. The compound of claim 4, wherein W is —CONHOH.

6. The compound according to claim 1, wherein the compound is selected from the group consisting of

B

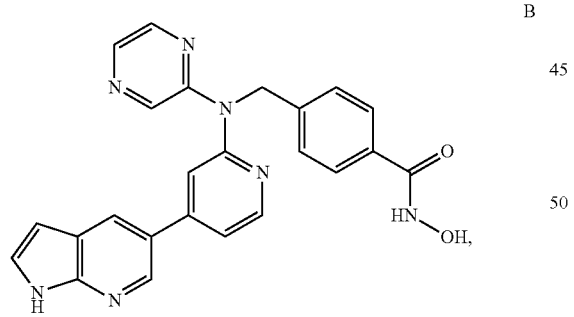

C

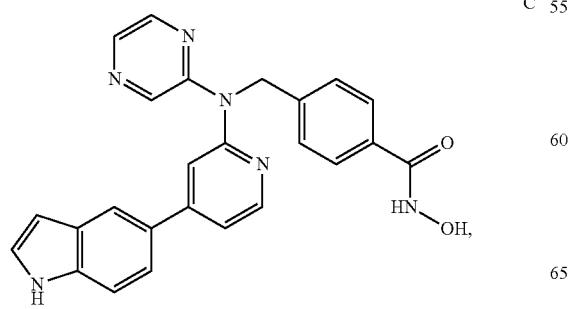

-continued

D

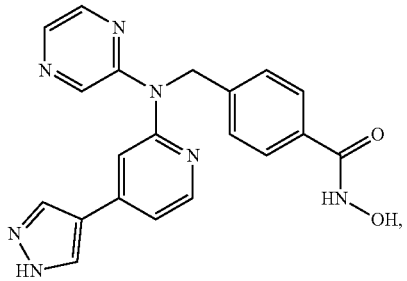

E

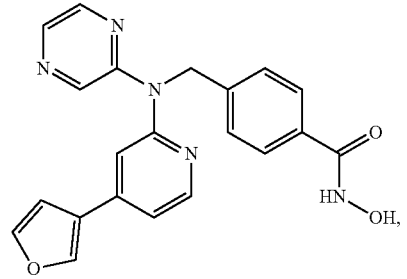

F

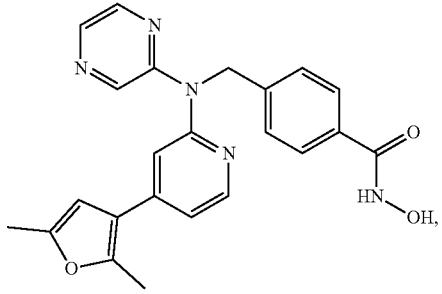

G

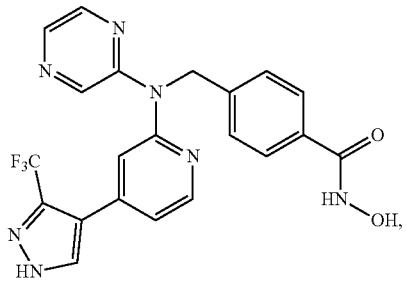

H

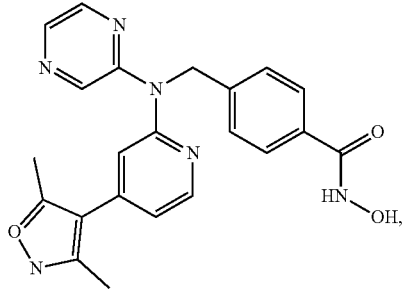

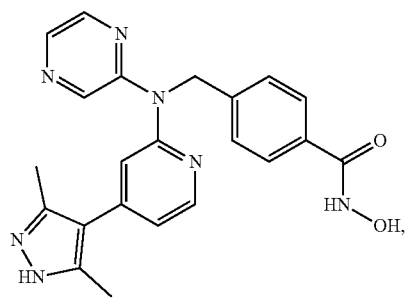
I
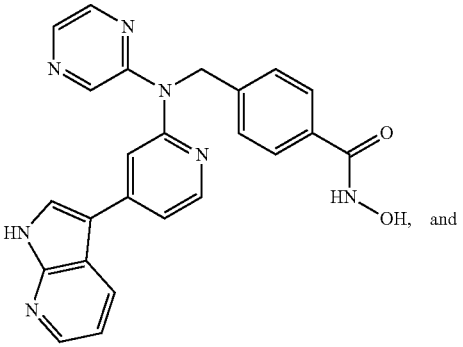
K
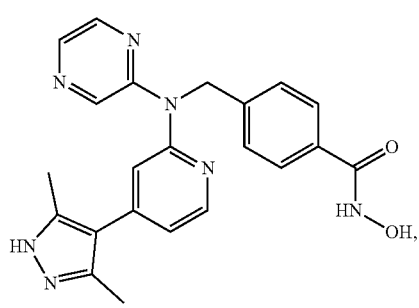
J
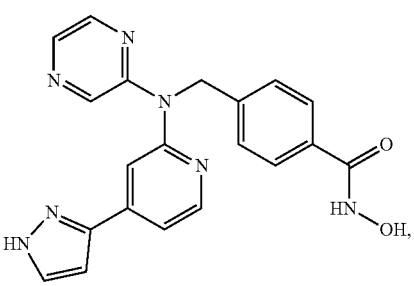
L
or a pharmaceutically acceptable salt thereof.
7. A pharmaceutical composition comprising a compound according to claim 1, and a pharmaceutically acceptable carrier or diluent.
* * * * *